United States Patent
Zhang et al.

(10) Patent No.: US 6,503,754 B1
(45) Date of Patent: Jan. 7, 2003

(54) ANTISENSE MODULATION OF BH3 INTERACTING DOMAIN DEATH AGONIST EXPRESSION

(75) Inventors: Hong Zhang, Carlsbad, CA (US); Jacqueline Wyatt, Encinitas, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 28 days.

(21) Appl. No.: 09/657,346

(22) Filed: Sep. 7, 2000

(51) Int. Cl.$^7$ .................. C07H 21/04; A61K 48/00; C12N 15/00
(52) U.S. Cl. .................. 435/375; 436/6; 436/377; 436/440; 536/23.1; 536/24.1; 536/24.5; 514/44
(58) Field of Search .................. 435/6, 375, 377, 435/440; 536/23.1, 24.1, 24.5; 514/44

(56) References Cited

U.S. PATENT DOCUMENTS

| | | | |
|---|---|---|---|
| 5,801,154 A | * | 9/1998 | Baracchini et al. |
| 5,955,593 A | | 9/1999 | Korsmeyer .................. 536/23.5 |
| 5,998,148 A | * | 12/1999 | Bennett et al. .................. 435/6 |
| 5,998,583 A | | 12/1999 | Korsmeyer .................. 530/350 |
| 6,001,651 A | * | 12/1999 | Bennett et al. .................. 435/375 |
| 6,008,048 A | * | 12/1999 | Monia et al. .................. 435/375 |

FOREIGN PATENT DOCUMENTS

| | | |
|---|---|---|
| WO | WO 98/09980 | 3/1998 |
| WO | WO 00/11162 | 3/2000 |

OTHER PUBLICATIONS

Sudhir Agrawal, Antisense Oligonucleotides: towards clinical trails, Oct. 1995, Tibtech, vol. 14, pp. 376–387.*
Yu Jen, Suppression of Gene Expression by Targeted Disruption of Messenger RNA: Availale Options and Current Strategies, 2000, Stem Cells, vol. 18, p. 307–319.*
Andrea D. Branch, A good antisense molecule is hard to find, Feb. 1998, Tibs, vol. 23, pp. 45–50.*
Chao et al., *BCL–2 family: regulators of cell death*, Annu. Rev. Immunol., 1998, 16:395–419.
Desagher et al., *Bid–induced conformational change of Bax is responsible for mitochondrial cytochrome c release during apoptosis*, J. Cell. Biol., 1999, 144:891–901.
Gross et al., *Caspase cleaved BID targets mitochondria and is required for cytochrome c release, while BCL–XL prevents this release but not tumor necrosis factor–R1/Fas death*, J. Biol. Chem., 1999, 274:1156–1163.
Kelekar et al., *Bcl–2–family proteins: the role of the BH3 domain in apoptosis*, Trends Cell Biol., 1998, 8:324–330.
Luo et al., *Bid, a Bcl2 interacting protein, mediates cytochrome c release from mitochondria in response to activation of cell surface death receptors*, Cell, 1998, 94: 481–490.
Sun et al., *Distinct caspase cascades are initiated in receptor–mediated and chemical–induced apoptosis*, J. Biol. Chem., 1999, 274:5053–5060.
Thompson, *Apoptosis in the pathogenesis and treatment of disease*, Science, 1995, 267:1456–1462.
Wang et al., *BID: a novel BH3 domain–only death agonist*, Genes Dev., 1996, 10:2859–2869.
Yin et al., *Bid–deficient mice are resistant to Fas–induced hepatocellular apoptosis*, Nature, 1999, 400:886–891.

* cited by examiner

Primary Examiner—Sean McGarry
(74) Attorney, Agent, or Firm—Licata & Tyrrell P.C.

(57) ABSTRACT

Antisense compounds, compositions and methods are provided for modulating the expression of BH3 Interacting domain Death agonist. The compositions comprise antisense compounds, particularly antisense oligonucleotides, targeted to nucleic acids encoding BH3 Interacting domain Death agonist. Methods of using these compounds for modulation of BH3 Interacting domain Death agonist expression and for treatment of diseases associated with expression of BH3 Interacting domain Death agonist are provided.

26 Claims, No Drawings

SEQUENCE LISTING

```
<160> NUMBER OF SEQ ID NOS: 174

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                                 20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                                 20

<210> SEQ ID NO 3
<211> LENGTH: 1105
<212> TYPE: DNA
<213> ORGANISM: Homo sapiens
<220> FEATURE:
<221> NAME/KEY: CDS
<222> LOCATION: (141)...(728)
```

<400> SEQUENCE: 3

```
gggcgggtag tcgaccgtgt ccgcgcgcct gggagacgct gcctcggccc ggacgcgccc      60
gcgcccccgc ggctggaggg tggtcgccac tgggacactg tgaaccagga gtgagtcgga     120
gctgccgcgc tgcccaggcc atg gac tgt gag gtc aac aac ggt tcc agc         170
                        Met Asp Cys Glu Val Asn Asn Gly Ser Ser
                        1               5                   10 ctc agg gat gag tgc atc aca aac cta ctg gtg ttt ggc ttc ctc caa       218
Leu Arg Asp Glu Cys Ile Thr Asn Leu Leu Val Phe Gly Phe Leu Gln
            15                  20                  25 agc tgt tct gac aac agc ttc cgc aga gag ctg gac gca ctg ggc cac       266
Ser Cys Ser Asp Asn Ser Phe Arg Arg Glu Leu Asp Ala Leu Gly His
        30                  35                  40 gag ctg cca gtg ctg gct ccc cag tgg gag ggc tac gat gag ctg cag       314
Glu Leu Pro Val Leu Ala Pro Gln Trp Glu Gly Tyr Asp Glu Leu Gln
    45                  50                  55 act gat ggc aac cgc agc agc cac tcc cgc ttg gga aga ata gag gca       362
Thr Asp Gly Asn Arg Ser Ser His Ser Arg Leu Gly Arg Ile Glu Ala
60                  65                  70 gat tct gaa agt caa gaa gac atc atc cgg aat att gcc agg cac ctc       410
Asp Ser Glu Ser Gln Glu Asp Ile Ile Arg Asn Ile Ala Arg His Leu
 75                  80                  85                  90 gcc cag gtc ggg gac agc atg gac cgt agc atc cct ccg ggc ctg gtg       458
Ala Gln Val Gly Asp Ser Met Asp Arg Ser Ile Pro Pro Gly Leu Val
                 95                 100                 105 aac ggc ctg gcc ctg cag ctc agg aac acc agc cgg tcg gag gag gac       506
Asn Gly Leu Ala Leu Gln Leu Arg Asn Thr Ser Arg Ser Glu Glu Asp
            110                 115                 120 cgg aac agg gac ctg gcc act gcc ctg gag cag ctg ctg cag gcc tac       554
Arg Asn Arg Asp Leu Ala Thr Ala Leu Glu Gln Leu Leu Gln Ala Tyr
        125                 130                 135 cct aga gac atg gag aag gag aag acc atg ctg gtg ctg gcc ctg ctg       602
Pro Arg Asp Met Glu Lys Glu Lys Thr Met Leu Val Leu Ala Leu Leu
    140                 145                 150 ctg gcc aag aag gtg gcc agt cac acg ccg tcc ttg ctc cgt gat gtc       650
Leu Ala Lys Lys Val Ala Ser His Thr Pro Ser Leu Leu Arg Asp Val
155                 160                 165                 170 ttt cac aca aca gtg aat ttt att aac cag aac cta cgc acc tac gtg       698
Phe His Thr Thr Val Asn Phe Ile Asn Gln Asn Leu Arg Thr Tyr Val
                175                 180                 185 agg agc tta gcc aga aat ggg atg gac tga acggacagtt ccagaagtgt         748
Arg Ser Leu Ala Arg Asn Gly Met Asp
            190                 195 gactggctaa agcttgatgt ggtcacagct gtatagctgc ttccagtgta gacggagccc     808
tggcatgtca acagcgttcc tagagaagac aggctggaag atagctgtga cttctatttt     868
aaagacaatg ttaaacttat aacccacttt aaaatatcta cattaatata cttgaatgaa     928
aatgtccatt tacacgtatt tgaatggcct tcatatcatc cacacatgaa tctgcacatc     988
tgtaaatcta cacacggtgc ctttatttcc actgtgcagg ttcccactta aaattaaat     1048
tggaaagcag gtttcaagga agtagaaaca aaatacaatt ttttggtaa aaaaaaa       1105
```

<210> SEQ ID NO 4
<211> LENGTH: 24
<212> TYPE: DNA
<213> ORGANISM: Artificial Sequence
<220> FEATURE:
<223> OTHER INFORMATION: PCR Primer -continued

```
<400> SEQUENCE: 4
agaagacatc atccggaata ttgc                                          24

<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
ggagggatgc tacggtccat                                               20

<210> SEQ ID NO 6
<211> LENGTH: 20
<212> TYPE: DNA
<213> ORGANISM: Artificial Sequence
<220> FEATURE:
<223> OTHER INFORMATION: PCR Probe

<400> SEQUENCE: 6
aggcacctcg cccaggtcgg                                               20

<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7
caacggattt ggtcgtattg g                                             21

<210> SEQ ID NO 8
<211> LENGTH: 26
<212> TYPE: DNA
<213> ORGANISM: Artificial Sequence
<220> FEATURE:
<223> OTHER INFORMATION: PCR Primer

<400> SEQUENCE: 8
ggcaacaata tccactttac cagagt                                        26

<210> SEQ ID NO 9
<211> LENGTH: 21
<212> TYPE: DNA
<213> ORGANISM: Artificial Sequence
<220> FEATURE:
<223> OTHER INFORMATION: PCR Probe

<400> SEQUENCE: 9
cgcctggtca ccagggctgc t                                             21

<210> SEQ ID NO 10
<211> LENGTH: 791
<212> TYPE: DNA
<213> ORGANISM: Mus musculus
<220> FEATURE:
<221> NAME/KEY: CDS
<222> LOCATION: (19)...(606)

<400> SEQUENCE: 10
agctacacag cttgtgcc atg gac tct gag gtc agc aac ggt tcc ggc ctg    51
                    Met Asp Ser Glu Val Ser Asn Gly Ser Gly Leu
                     1               5                  10
```

```
ggg gcc aag cac atc aca gac ctg ctg gtg ttc ggc ttt ctc caa agc         99
Gly Ala Lys His Ile Thr Asp Leu Leu Val Phe Gly Phe Leu Gln Ser
            15                  20                  25 tct ggc tgt act cgc caa gag ctg gag gtg ctg ggt cgg gaa ctg cct        147
Ser Gly Cys Thr Arg Gln Glu Leu Glu Val Leu Gly Arg Glu Leu Pro
        30                  35                  40 gtg caa gct tac tgg gag gca gac ctc gaa gac gag ctg cag aca gac        195
Val Gln Ala Tyr Trp Glu Ala Asp Leu Glu Asp Glu Leu Gln Thr Asp
    45                  50                  55 ggc agc cag gcc agc cgc tcc ttc aac caa gga aga ata gag cca gat        243
Gly Ser Gln Ala Ser Arg Ser Phe Asn Gln Gly Arg Ile Glu Pro Asp
60                  65                  70                  75 tct gaa agt cag gaa gaa atc atc cac aac att gcc aga cat ctc gcc        291
Ser Glu Ser Gln Glu Glu Ile Ile His Asn Ile Ala Arg His Leu Ala
                80                  85                  90 caa ata ggc gat gag atg gac cac aac atc cag ccc aca ctg gtg aga        339
Gln Ile Gly Asp Glu Met Asp His Asn Ile Gln Pro Thr Leu Val Arg
            95                 100                 105 cag cta gcc gca cag ttc atg aat ggc agc ctg tcg gag gaa gac aaa        387
Gln Leu Ala Ala Gln Phe Met Asn Gly Ser Leu Ser Glu Glu Asp Lys
        110                 115                 120 agg aac tgc ctg gcc aaa gcc ctt gat gag gtg aag aca gcc ttc ccc        435
Arg Asn Cys Leu Ala Lys Ala Leu Asp Glu Val Lys Thr Ala Phe Pro
    125                 130                 135 aga gac atg gag aac gac aag gcc atg ctg ata atg aca atg ctg ttg        483
Arg Asp Met Glu Asn Asp Lys Ala Met Leu Ile Met Thr Met Leu Leu
140                 145                 150                 155 gcc aaa aaa gtg gcc agt cac gca cca tct ttg ctc cgt gat gtc ttc        531
Ala Lys Lys Val Ala Ser His Ala Pro Ser Leu Leu Arg Asp Val Phe
                160                 165                 170 cac acg act gtc aac ttt att aac cag aac cta ttc tcc tat gtg agg        579
His Thr Thr Val Asn Phe Ile Asn Gln Asn Leu Phe Ser Tyr Val Arg
            175                 180                 185 aac ttg gtt aga aac gag atg gac tga ggagcccgca caagcccgat              626
Asn Leu Val Arg Asn Glu Met Asp
        190                 195 ggtgacactg cctccagagg aaccgcgacc atggaaagac cttggcctga agacaggtcc      686
cagagaacag ctgtctccct atttccaggt ggtgggaacc ccaagctggt gattcactgg      746
acatctctgc gttcagcttg agtgtatctg aagagtttac gccgg                      791

<210> SEQ ID NO 11
<211> LENGTH: 20
<212> TYPE: DNA
<213> ORGANISM: Artificial Sequence
<220> FEATURE:
<223> OTHER INFORMATION: PCR Primer

<400> SEQUENCE: 11
tcgaagacga gctgcagaca                                                   20

<210> SEQ ID NO 12
<211> LENGTH: 23
<212> TYPE: DNA
<213> ORGANISM: Artificial Sequence
<220> FEATURE:
<223> OTHER INFORMATION: PCR Primer

<400> SEQUENCE: 12
tggctctatt cttccttggt tga                                               23
```

<210> SEQ ID NO 13
<211> LENGTH: 19
<212> TYPE: DNA
<213> ORGANISM: Artificial Sequence
<220> FEATURE:
<223> OTHER INFORMATION: PCR Probe

<400> SEQUENCE: 13
cagccaggcc agccgctcc                                                        19

<210> SEQ ID NO 14
<211> LENGTH: 20
<212> TYPE: DNA
<213> ORGANISM: Artificial Sequence
<220> FEATURE:
<223> OTHER INFORMATION: PCR Primer

<400> SEQUENCE: 14
ggcaaattca acggcacagt                                                       20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
gggtctcgct cctggaagct                                                       20

<210> SEQ ID NO 16
<211> LENGTH: 27
<212> TYPE: DNA
<213> ORGANISM: Artificial Sequence
<220> FEATURE:
<223> OTHER INFORMATION: PCR Probe

<400> SEQUENCE: 16
aaggccgaga atgggaagct tgtcatc                                               27

<210> SEQ ID NO 17
<211> LENGTH: 18000
<212> TYPE: DNA
<213> ORGANISM: Homo sapiens
<220> FEATURE:
<221> NAME/KEY: CDS
<222> LOCATION: (2144)...(2155)
<221> NAME/KEY: CDS
<222> LOCATION: (8247)...(8457)
<221> NAME/KEY: CDS
<222> LOCATION: (12772)...(12911)
<221> NAME/KEY: CDS
<222> LOCATION: (14031)...(14243)
<221> NAME/KEY: CDS
<222> LOCATION: (16669)...(16680)

<400> SEQUENCE: 17
cctgggtatc caagtcgccc tggcagagaa acactgcatg agacacggcg ttagggtctg           60
gtgggagact caccacagtg ccaaggtggc tgcagtttgc ttgtgacatg ggcgtgtatc          120
tgagtgtgaa ggaagctggt ttttgtgagc tgcctcccga gctcagaggt gacagtgggc          180
actttcccca cagagacccc tgaagttgtt ccttggagaa caaagtggtg aggggcgggg          240
attccagacc ttgaggcaga agctagggtc tggtccactg ttctgtggac tgggcagtgg          300
ccctgggagg tgccgtggcc tctgtggcct gtttcctggg gtgggtctg tcttgcgctt           360 tgtctcttgt gggtgcagac tcccttcct ctgctgtgga gccggcagat ggccccggag           420

-continued

```
ccagatcctg gtgcctccct gtccacatgc agctcagtca tttgctcttg gtcccttcct    480
atgaaatgca cggccacaca cagccagggt ttctcctggg ctccccagag ggagagtagg    540
gtgcagcctg caacagtgca gggtcccag gcctgtgtga gccccaggt ggggaggtgg     600 gtgatgcgca tgtcagtgct acctcctgcc acctcctctc tgcctgggca caggcttct    660 cctctgtttg cttttatttt cctatgtatt caggaaccat gtgaaattgc caatgcttgg   720
ttttgtccta caaatggcc atttcatttg gttcaacctg atattgtgtc tacacacaca   780
cacgcacaca cacacacaca caggcaaata ctttttaaaa caggattatt ctattcacag  840
tgttctgtag aaatttgtgt tcagtctttt tttttttttt tgagacggag tctcgctctg  900
tcgcccaggt cggactgcgg actgcagtgg cgcaatctcg gctcactgca agctccgctt  960
cccgggttca cgccattctc ctgcctcagc ctcccgagta gctgggacta caggcgcccg  1020
ccaccgcgcc cggctaattt tttgtatttt tagtagagac ggggtttcac cttgttagcc   1080
aggatggtct cgatctcctg acctcatgat ccacccgcct cggcctccca agtgctggg   1140 attacaggcg tgagccaccg cgcccggcct cagtctttt aagacagctt actgtactga   1200
tgccgcacag atctttttt ttttcgaga cagggtttca ctctcgccca ggctggagtg   1260
cagtggtgca atctccgctc actgcagcct ccacctcctg ggtgtaagtg atcctcctgc  1320
ttcagccccc caagtagctg ggcccacagg gcttgcatca ccacacctgg ctaattttgt  1380 attttttgtag agatggggtt tcaccatgtt ggccagactg tcattctttt tgagatgga   1440 gtctcgctct gtcgcccagg ctggagtgca gtggcgtgat ctcggcttac tgcaacctct  1500
ccctcccaag ttcatgccat tctcctgcct cagcctcccg agtagctggg actacaggcg  1560
cccgccacca cgcccggcta atttttttgta tttttagtag acagggtt tcaccgcatt  1620 agccagggtg gtctcgatct cctgacctca tgatccaccc gctcggcct cccaaagtgc   1680 tgggattaca ggcatgagct actgcgtcca gccggaagat ttaattttt aattgtcaaa   1740 tccattctct ctctctataa acattttaca tttatgata ataaaataat ttgtgagccc  1800
acggccccgt ttccctgatg cctgaggtct tcctggggcg gcatgggagg gctgaattca  1860 ggtgcgggt cggccccagg gcactgagcg cctgggtgag tatctggaat gaggaaaaca   1920
aagcttggct cccgccaagg agaaagaaac tcaggatgcg gggctcaggc caggacctcg  1980
gctcagccgc catttctgga gcacaggcca gcttcgtcgt cctcccgagg ggtcctgacc  2040
agggcttccc aggagcggcc gcccactctg tgtgtcccctt tccaggtcgc cactgggaca  2100
ctgtgaacca ggagtgagtc ggagctgccg cgctgcccag gcc atg gac tgt gag    2155
                                                    Met Asp Cys Glu
                                                     1 gtcagaggcc agatcccctg cgggtgcctt gtgggggggcg gggtcgaggg gtaagggcct  2215 gcgtgtcccc caccacgcat ccctgagggc tgaggctgag cccgcctggc ccttaccaca   2275 gctcggcaca gacgaaccc gcccagcccc ttcactgaag caggcgggag ccgggaagtc   2335 ctacctttcc ctgtcctgcg ccttcctcgc actccgcttg tggtgcagcc cctccacacc   2395 gcgcctgggg ctaactgcaa gggcgagggg gctttgggtt taagaccatt taacagccat  2455 aggctgtggg tccagcacct ttgggaggcc aaggcaggag gattccttga ggccaggagg  2515 tcgaggctac agtgagctgt gattgtgcca ctgcactgca gccctgtcca aacaaacacg   2575 aaagagattt aagaagaaga aagggggcat tagataagca cttcatataa ttctctcaac   2635 tgtaaaagca agacaatact taccttgtct aaccaatgcc attgctatga ggagcaaata   2695
```

```
aatcaataaa ggtcaaataa aagtactgta aactgtaagg tgtttcaaaa attttttaac    2755
ccactggatt taaatttccc ttcatagctg ggcgaggtgg cttaggcaca taatcccagt    2815
gacttgggag gcagaagcga gaggattgct tgaagccagg agtttgattg agacaaacct    2875
gggcaacata gtaagacccc gtctttataa agataaaagc ggtggagttc tgggagggga    2935
gcccggagcc cccgccttca gcaggacgct ccctggatgc ttccttgtct ctccttccct    2995
ttaaatggtc tggggagaga aaaatcacag cacacgggtg ctctctccca cccgctgcat    3055
cacatcctcc tcccctccct cctgccgaat tctgcagcct ctgggcgcct cacgctgtcc    3115
tggcagcctc tgggaaggca tctgcgaagt ctaatgcctt ggcacttagt gactgtgtcg    3175
cagttcctga gcatggagag cacccggcac ccaggaggtt ctcaagctgc ccctactggg    3235
ggtcctttcc aaaggtgggg acggtgtgga tttcagcgtg gtggctggag ggctgaggca    3295
gtggctcgag tttgatgtta gttacataaa cagaggagat tgcaggagct cccccggccc    3355
tgatccaggc ttgttgtcag tgtccaaaag accactctgg gtgccactgt cccttcccac    3415
ctgccgctgc tgttccggct tcgcgctctg gcggcctccg caggtagaac accaccgtca    3475
cccgcgcagc gccctgactc gccggaggag gcgcctgccc tcccgcccgc ctctcccgg    3535 cccccctcagt gagggagggt ggacgtcgcc actccccttt cttgccttcg gagtgaggaa    3595
gcggaggcag cagtacggca gcccgcccag ggccacagag ctggggtcac agcgaaacac    3655
tccgaaactt tcttttcaat tatagggttc agccttttt cccatcataa ctttaattct    3715
gtgtagatac ttctattttt tattttatt ttttttttg agattgagtc tctgtgtcgc    3775
ccaggctgga gtgcagtggc acgatctccg ctcactgcag gctccgcctc ccgggttcag    3835
gccattctcc tgcctcagcc tcccgagtag ctgggactac aggcgcccgc caccacgccc    3895
ggctcatttt ttgtatctta gtaaagacgg ggtttcaccg tgttagccag gatggtctcg    3955
atctcctgac ctcgtgatcc gcccgtctgg gcctcccaaa gtgctgggat tacaggcgtg    4015
agccaccgtg cccggcctta ttattattat tttttgaga cgcagttttg ctctgtcgcc    4075
caggctggag tgcagtgatg tgatctccgc tcactgccag ctccgcctcc caagttcatg    4135
ccattctcct gcctcagcct ctcgagtagc tgggactaca ggcgcccacc accacgcccg    4195
gctaattttt tatattttag taaagacggg gtttcaccgt gttagccagg atggtctcga    4255
tctcctgacc tcgcgatctg cccgcctcgg cctcccatag tgctgggatt gcaggcgtga    4315
gccaccgcac ctggctaatt tttgtatttt tagtagagat ggggtttcac catgttgccc    4375
aggatgttct cgacctcttg acctcatgat ccgcccgcct cggcttccca aagtgctggg    4435
attacaggcg tgagccaccg cgcccggcca gcaccatctt ttccttttcca ctggaactga    4495 tcttattatt tttgcctcca ttagatcatt tttgtaacat gtcttgcagg atttactgtc    4555
ttgatcgttt ctcttaacat atttttttcc tgtgatctaa aaagataaaa aactatcaat    4615
tcttttatca aaagtggatc tagaggctgg gcatggtggc tcacgccagt aatcccagca    4675
ctttgggagg ccaaggtggg cagatcacct gaggtcaaga gctccagacc agcctggcca    4735
acatggtgaa gccccatctt tactaaaaat acaaaaatta gccaggcgtg gtggcacgtg    4795
cctgtaaccc cagctacttg ggaggctgag gcaggagaat ccattgaacc tgggaggcag    4855
aggttgcagt gagctgagat ggcaccattg tactccagcc tgggcaacag aatgagactc    4915
tgtctccaaa aacaaagtgg atctagaaga tcaaaaaagg gcatgattcc atattggcac    4975
agcacaagcc ctattcttgg aattaaatgg catccatctt ccgagcccac tcctgtcctg    5035
cagggccggc ccagcctgtc cctgaggcac tggtccagac aggagcctgt ccacacagct    5095
```

```
gtccactcag tgggcccagt gcttggcttc acggtcactt gcggcaccta gacctcctct    5155
ggcaggtgcc attctttcct ctccctccct gccgcctcga gtctttattt tctgtgggat    5215
cttgagtttg ataacctgac ctgctgtggt ggcagcaccc ctctgtgtcc agattctgga    5275
tgccaattta ccaagcgcag gtcaaaaaga agtccttggg cagcggctgc ctgcgttagc    5335 ttcttgggc tgctgtaggc ggttccaagc aggagagtgg ctttaaacaa cagatgcgga     5395
tcccctcccg gttctagagg cccaaaggct ggaatcccat gttgcccggc tgcttccttc    5455
tggggcgctc tcctggctcc tgtggctgcc tctgtcttca catggcgtcc tctctgtgtg    5515
tctctgctta aatctccctc tcctttctct tacaaagaca ccagtcattg gatttagggc    5575
ccaccctaat ccaatatgac ctcatcttaa cttgattaca tctgtaaaaa ccttatttc     5635 aaataaggtc acattgacag gtacttgggg ttaggacttg cgcttttctt tttgggtgac    5695
acagcttagc ccagcactaa ctgtgtcacc aggactgtcg cttgaggcag gaatgaagca    5755
catcctgttt gtaagctgtc ttgtgccatg cggctgctcc gtacaagaat tgttaggaat    5815
tgatgcagtg gaattttgca tacagttttt cctctcttca gaaacaactt ggagaagta    5875 aaggctgaat agcaatacac aagcacctta tttttatttta ttttagattc aggggcacgt   5935
gtacatgttt gtcacatggg aatattgtgc actggtgggg actgggcttc cggtatcgca    5995
tggagaggga ctctttctgc gctcccccgc ccccgcctcc ctactgtaaa gtgcccggtg    6055
cctgctctct ccatcttcgt gtccatgggc acccattgtt tagctcccac ttataagtga    6115
gaacagtcag tatttgattt tctgtttctg agttagttca cttagggtaa tggcctctag    6175
ctccatccgt gttgctgcag aggacatgat tttattcttt tttatggctg cagcaataca    6235
caagctcctt attttttattt atttatttat ttattttgt tgtttgtttg tttgttttga    6295
gacggagtct ggctctcgtc ccccaggctg gagtgcaatg gcgcgatctc ggctcattgc    6355
aacctccacc tcccgggttc aagcgattct cctgcctcag cctcccaagt agctgggact    6415
acagacgccc gccaccaggc ccggctaatt tttgtatttt tagtagagac aaggtttcat    6475
catgttggcc aggctggtct caaactcctg acttcgtgat ccgcccgcct cggcctccca    6535
aagtgctggg attacaggcg tgagccaccg cgcccggcca agctccttat tttaagcatt    6595
ttttttttct tttttgagac agggtttcac tttgtcaccc aggttggagt gcagtggtgt    6655
gatcatggct cattgcagcc tcaaacttct gggctcaagt gaccttcccg cctcagtctc    6715
atgagtagct gggactgcag gtgcatgcca ccttggctaa ttttttatttt ttgtagagat    6775 ggggatcttg ttgccaggct ggtctcaaat tcctgggctc aaacgatcct cctgcctctg    6835
cctcccagag tgccgggatt acaggcatca cctagcaaag cattaaaaca atttgctgct    6895
gggtgcagta ggtcacacct gtaatcccag cactttgaga ggccaaggag ttgggggag    6955 ttgggggcg gcggatcac gaggtcagga gttcgagacc agcctgacca acatggtgaa     7015
acctcgtctc tactaaaaat acaaaaatta gccgggcgtg gtgatgcaca cctgtaatcc    7075
cagctactca ggaagctgag gcgggagaat catttgaacc caggaagcgg aggttgtagt    7135
gagccgagat cacaccactg cactccagcc tgggtgacag agcgagactc catctcaaaa    7195 caaaacaaa aacaaaaaaa caatttgccc tgtaagaact gtcctctaaa agtttttggt     7255
ttttctaatg aaaaatatta tggacttaga gaatagaaat aaatttctgc ctacacttcc    7315
atcttccctc ccacccttct ctggcagccc aggaggtctt tttgtgtgaa tctgcgcaga    7375
tctcagcgtc cctgcccttc tttgtgtttt gttctctctt ccaccttagg tctttctctg    7435
```

-continued

```
gtctgggcac acccagctgc agggctcacc tttgcctgta agaatacagc ccccaaacac    7495
agtcagtacc ccaagaacag tccctgccat ctctggcggc acagatgctg gccaagctgc    7555
agctgccagt gctgcccagg gagctggaga gctgccggcc aagagcccag ccctctggg     7615 tagagcagga gccagtgcca ccactccctg tgggattcgg attaaggaca cacccaccca    7675
aagtaaacca agcttggcca aaggcaggtg cccagctgtg gtcaccactc cgcagtagtt    7735
actgaaaatc ttccatctgc ccaatacctc cctgagcccg tgaaggagat gagcggaaag    7795
aggctccgcc tgttggaagc acagccagga aaggtgggct cagattgctg aagcctgcag    7855
gggaacttga agaaagcgtg ccagcacagg atggcggatg atgcccgcat gacactcgct    7915
cgcctccccg aacagcctg tggccttctc acctagtggg aagctcccca gccgcgtgtt     7975
tcaggaggtc cagcagattc ctctgcagag gaatccctt ctgcagagtc ggggctcgct     8035
ccctgccatc tacgggcagt gctgcttaaa gctgtggctg cagaccttgc ctctgcctgt    8095
tgagacctcc tgcagggccc tccagcccac agggtccctc agctctctgg gacctgtgag    8155
gctctttggg ccagctgcaa ctggagctct ttgcaggagg ggcctctggc ctggctgaag    8215
tcccggcttc ctgactcccc tttcccctca g gtc aac aac ggt tcc agc ctc      8267
                                   Val Asn Asn Gly Ser Ser Leu
                                    5                   10 agg gat gag tgc atc aca aac cta ctg gtg ttt ggc ttc ctc caa agc    8315
Arg Asp Glu Cys Ile Thr Asn Leu Leu Val Phe Gly Phe Leu Gln Ser
        15                  20                  25 tgt tct gac aac agc ttc cgc aga gag ctg gac gca ctg ggc cac gag    8363
Cys Ser Asp Asn Ser Phe Arg Arg Glu Leu Asp Ala Leu Gly His Glu
    30                  35                  40 ctg cca gtg ctg gct ccc cag tgg gag ggc tac gat gag ctg cag act    8411
Leu Pro Val Leu Ala Pro Gln Trp Glu Gly Tyr Asp Glu Leu Gln Thr
45                  50                  55 gat ggc aac cgc agc agc cac tcc cgc ttg gga aga ata gag gca g      8457
Asp Gly Asn Arg Ser Ser His Ser Arg Leu Gly Arg Ile Glu Ala
 60                  65                  70 gtaggcggcc ggccccacct ccttccccaa agctgggctt ctctgtcgcc agtaacattc    8517
agggagcctc agggctggaa gggaccccg ggatcactct gcctctgcag tttcagctgc     8577
cacgtacgct ggtatcactt aatcacttga ctggtctcta cttgattccc tccagtgctg    8637
ctgaactcac tgcctaccat ttttgggtga ctctgttaga aagttcttcc tttctgttga    8697
gacagaatct catgtactgg tcttgagtcc cttgtctgga ccaacataga atggtgtttt    8757
tatccaattt tccaaatgtg attctgatac aaagattgca gaccacttgt ctggattata    8817
taacccaagg ggttctcaca cttggccttg tatcatttca aggacctgga gctttaaatg    8877
ctggtgcctg catctcacct ccagagattc tgattggttg gtctgggcat tgctgggtct    8937
gggcaaagcc cccaggtggc actaccggtg cggcccctgc ctccccaagc aggcctggct    8997
gactgtccca ttgattgagg cccactggtt tcacagtgac ttttgcactg tctataccctg   9057 acatatttcc tttcatacat tatgctccgt gattacctat acaagaacac agaagtattt    9117
ggaacctcat ttccaggtga ggaaacccag gtccagcaaa gggtaaatga ctagctccag    9177
atcacacagc ttgtggccat gttaccactg ggacatgggg ccaggcccct tcttgaggtg    9237
ggcctcagcc gccctccac tgtagggcac tgactccagg tcaccatggt ttccagactg     9297
ttcacctttc ctgttgctga tccctgcact ctcctccagc ctccagctcc actcccctt     9357 gccagggggc tgcttctatg gacagggggct gtcccgagtc gaggctgggg gcgagtggag   9417
gctcacccac ttccagatcc agccctgcga cgctggcttt cagtagtgtg cacattggaa    9477
```

-continued

```
ttacacgaga aacctttcc aaatgcaggc cttgggccct actccagctg cctgcatcag    9537
gctgttttag ggcgggagac tgcccagagg attctgacgc aggtagaatc cctgccctga    9597
aagcctgcag ggatccccgg accctggtcc aggccttcca agctcaaggg ttgcactgcc    9657
ctctggtggc tgtgggggag accaacagct gacccagcct tctgcctccc gcctgtctta    9717
gatcaggtgc ttgaggacgt ggctggagtt ccccactaga ccggggtggg ggtggggggtg   9777
gggggtgggg ggaggtgtct gagaatgtct ctgccttcta atccagccag catatcttct    9837
ggctcgccct gaactgagga gaaacccag atccctttgg gaaggtccag gaagggcagg    9897
agtggacagg cacagctctg ctgtcagcac tgctgtgggg gtgactgtag ccccagtctg    9957
ccctggtgtt tttctctcgc tcttctccat gccggccttt gcctctagac tgagaaaccg   10017
gggttgactc aagtggcacc tgcaaaagtg atcatggcag ttcacttagc ctgcaggtga   10077
cagggactgt gaatctagtc cctggcgagc ctggaaagag gggcaaggta gaggctctgg   10137
ctgccggggt ttctttggtg agtccgttca ctcggctgga cacagacgga tcaggaaaga   10197
ttcctgttgc tactcggctg gtggccagag ggagagagga cgtgtccgta actgaagcaa   10257
ggtggataag cttcgggaac gagcgaggca cagattcggt gctggggag tgatgaggtg    10317
ctggaggagc tgggtgctct gctctgcagg gaatcaggaa aactttgggg ctgcagctcc   10377
aattgagctg ggccttgggg gttgggtatg tttggttcct tggaaactgg gaagagggaa    10437
tggccatctt ttaagcaaaa gcccagcggc tataaatgct acagtgaggc tgggtgcagt    10497
ggttcacgcc tgtaatccca gcactttggg aggccaaggc aggtggatca tgaggtcagg   10557
agttcaagac caccctagcc aagatggtga accccgtct ctactaaaaa aaatatataa    10617
aaattagcca ggcggggtgg cgggtgcctg taatcccagc tacttgggag gctgaggtag   10677
agaattgttt gaacccggga agcggaggtt gcagtgagct gagattgtac cactgcactc   10737
cagcttgggg aacagagtga gactatgtct tgaaaaaaa aagaaaaaa aaagctacag    10797
tgagtagttg agtttgccta ggaagcgtgg aagttaagtc agacgtactt tcaggctggg    10857
tcatgacttg tcacttaagc agagatgagc acttgagagg ttttgaagag aagtgatgtgt   10917
gcagccttac tgcatgttcc atggacagac tccaggagg ccgtgaaacc cccagagcac    10977
agcttctaag aacgtgccca ctccttagca cgtcacttct cccaaccctg ccctgctctg   11037
aggtctgtgc tgtgaaggtg gccgagtaga ctggacggca gggagtgggg ctgtcatcat   11097
cagatgagag ctaaggggac ccccaccagg gtggcggcaa tggcagaggg taggcaaaac   11157
gcttgtattt gcaacataag gtgagatttg acagctgacc gagggtggga gcagcagcca    11217
aaaccaaaaa agccagaggg aagttgcaag cacagaaaaa atagaagatt taatgggaga   11277
aataacaata gctggcatct attgaacact tactgggagc taggtacagg gcccattcat    11337
tcattcatgc aattaaaact ttttttaaga aacgggtct tgctctgttg cccaggctgg    11397
agtgtagtgg tatgatcaca gctcactgca gccttgaatt cctggcctca aggagtcctc    11457
ccacctcagc ctcctgtgta gctgggatta taggtacgtg cggtacacct ggctcccttt    11517
aaaagttttt tgtagaggca gggcacagtg gctcacacct gtaatccagc cactttggga   11577
ggccaaggca ggaggatcac aaggtcagga gttcgagacc agcctgacca acatggtgaa   11637
acccgtctct acttaaaata caaaaattag ccgggtgtgg tggcgggcgc ctgtaatccc   11697
agctactcag gaggctgaag catgagactt gcttgaaccc aggaggcgaa ggttgcagtg   11757
agccgagatc gcgccactgc actccagcct gggtgacaga gcaagactcc gtctcaaaaa   11817
```

-continued

```
aaaaaaaaaa gtttcttgta gaggcagggc cttgctttgt tgctggtgca atcacggctc    11877
actgcatcct ctaactcctg gccttaagca atcttctgtc ctcagcctcc caaagcactg    11937
ggattacagg catgcatgac cacacctggt ccctgccatt gtttattgag cacctactga    11997
gtgccatgta ttaagtgctg ggtatttgtc agtggacaaa acagattaaa aaaatcacag    12057
cccttaggga gcttaccttc tggcaggggc gtcagacaat aacacagcaa gtgctgagga    12117
agaaacggag gcggcaggga gcgtggcagt tgagcgtggc cttcatggag ctgcgacagt    12177
ggtactcggg caggggcagc acggaggctg tcgccagag gaggaggact gaggggcaag     12237
ggggagagct ctggttggaa aggcagggga gattctccag ggccttgccg gtgccagtga    12297
caactggggt tttcctgaga cgggactgcg aggaatgggg gctctcaggc ttgagagggc    12357
aaaagtgggt ctgggatgcc gtctgcccac agagccccttt ccccaacggc tgcccaggcc   12417
aaggccaacc ctgttgggtt gtgtggtgtg agccatgaag ccgctgccag gcttgtacct    12477
caggcgtggt cgtgatgccc cagcttcacc ggccctgcct gtggggacgt ggtgcctgtg    12537
tgcgggagcc tgggcctcag ccgaggccct gagctccggc actgcccaga acccagctca    12597
gcgctggtac tcagcccgcc cgctgtggcc ctggtggagt ggagcacgtg cccagtgggg    12657
gctggccttg tcccatcgcg gacctgtcct ttcccgggc agggtggtgt gggagagggt     12717
atcagggaca ttttctgagt ctgctctgtc tctgccgccc ctgcctgaac acag at       12773
                                                          Asp
                                                          75 tct gaa agt caa gaa gac atc atc cgg aat att gcc agg cac ctc gcc     12821
Ser Glu Ser Gln Glu Asp Ile Ile Arg Asn Ile Ala Arg His Leu Ala
        80                  85                  90 cag gtc ggg gac agc atg gac cgt agc atc cct ccg ggc ctg gtg aac     12869
Gln Val Gly Asp Ser Met Asp Arg Ser Ile Pro Pro Gly Leu Val Asn
            95                  100                 105 ggc ctg gcc ctg cag ctc agg aac acc agc cgg tcg gag gag              12911
Gly Leu Ala Leu Gln Leu Arg Asn Thr Ser Arg Ser Glu Glu
        110                 115                 120 gtgagtgagg gcctgaggac cgcgtgggcg ggcaagtgag ccaagggggc ctgtcccctg    12971
cctctcacca ggcagcccac tgtcccgtga ggccactcaa ctcgtgactg tcaggtccag    13031
aactctgacg aagtaactgg acgtagggta tggttcattg ccttgcagaa gatttcagct    13091
ggttgacatc gaggaaacct gaaccttaaa tcagagtaaa gagtttaggg gtaaaagcct    13151
ctaaaagatg aacgaagcat gtttggccaa cagaagaaac agacgcttcc tttggttgta    13211
gggagtttaa taatggtgcc agtgagaacc gtaagccctg ggagtggtgc ctgctgctct    13271
gctgagctcc ttggttggaa tccacacaac tttctgagct ctaccatctg cttggcactg    13331
ttggggatac aagattggtc cggggcactg tgtccccaga acacttagcg gaaagaacta    13391
catcctccca actgccaaat gcaggcctgt agcggtagga gctgagagga gagaaagttc    13451 cacttttttcg actctaccag ctgaaaatgc aggcgtcctc acctcctaga aatccaatca   13511
tgcttctgtt cagtggggcc agcctgtgat gtcccagcag ctgcctagaa cgcaggagtg    13571
gctggcgcac tccatgtaa ctctgcatgt gcgccgaccg cctgacggtc cttgccagcc     13631
ttgtagtctg tctagtgtcc cccaggaacc cccttcctcc tgtccattca gctaggtctg    13691
caccaataaa atgggcctaa ggcgtcgcag gtggtcacta gttctggact cgaagtgcct    13751
tgggcgcagg gatgacccag gcttcttgta tcccatcacc gtctaacagt gggcacatgg    13811
gctcaccaca catgcgtttg cttaccgagc ccctgcagg gagtgattgc agtcttccct     13871
ttccattgcc tctcagaact caactgtttc tcattctttc cgcccagcag ccctggatac    13931
```

```
ttaataagta ctttgaagtg cttcttcata ctggggactg tctttccttt gagagggaag    13991
agtattagta aaccaggttc tgtgtgcccc tctgtgcag gac cgg aac agg gac        14045
                                           Asp Arg Asn Arg Asp
                                                           125 ctg gcc act gcc ctg gag cag ctg ctg cag gcc tac cct aga gac atg      14093
Leu Ala Thr Ala Leu Glu Gln Leu Leu Gln Ala Tyr Pro Arg Asp Met
            130                 135                 140 gag aag gag aag acc atg ctg gtg ctg gcc ctg ctg gcc aag aag          14141
Glu Lys Glu Lys Thr Met Leu Val Leu Ala Leu Leu Ala Lys Lys
        145                 150                 155 gtg gcc agt cac acg ccg tcc ttg ctc cgt gat gtc ttt cac aca aca      14189
Val Ala Ser His Thr Pro Ser Leu Leu Arg Asp Val Phe His Thr Thr
160                 165                 170 gtg aat ttt att aac cag aac cta cgc acc tac gtg agg agc tta gcc      14237
Val Asn Phe Ile Asn Gln Asn Leu Arg Thr Tyr Val Arg Ser Leu Ala
175                 180                 185                 190 aga aat gtaagaaccc ttgaggtcag ctccttccct gctgccgcc catgcccttt        14293
Arg Asn tctctggaag gttgagaagc ccagcggggc ccctgcctct gatgccagca caagggttac    14353
aggctgtcct gctcgggttt ggttttgctg ttgtgagcta gaaagctgtg tgtaaaggtg    14413
acgaagagca cccagagtcc tttggagctt tagcagctta ctattggaga catgctccat    14473
tcagaggggt ggcaaaggct cacgtcacac tcctggtggg gtcctcaagg cacaagcagg    14533
tacagagtgg aaggaagggg ctggagggct cacaatgagc ttttcagacc tctcaccttg    14593
ccataaaaaa taagtgtaat gtggccagtg cggtggctca tgcctgtgat cccactgctc    14653
tgggaggcca aggcaggtgg atcacctgag gtcaggagtt ccagaccacc ctggccaaca    14713
gggtgaaagc ccgtctctac taaaatacaa aaattagccg gcatggtgg cgcacacctg     14773 tagtcccagc tactcaggag gctgaggcag gagaactgct tgaaccctgg aggcagaggt    14833
tgcagtgaac tgagatcgca ccactgcact ttagcctggg cgacagagca agactccatc    14893
tcaaaaaaaa ggtgtaatgt gaaccaaaac gagtagtcaa aaaagggggg gaactgtctg    14953
aaatcttttc cagagcacat ctgtcccata accaggtatt acaagtcaca gtctaaaggc    15013
tgggcatggt ggctcaagcc tgtaatccca gcgatttggg aagcagaagc agtgggattg    15073
cttgaggcca ggagtttgag acaaaactga gcaacatggc gagaccctgt ctctaaaaaa    15133
tttataaaaa taattagctg agggccaggc gcggtggctc acgcctgtaa tcccagcact    15193
ttgggaggcc aaggcaggcg gatcatgaag tcaggagttc aagaccagcc tggccaagat    15253
ggtgaaaccc cgtttctact aaaaatacaa aaaaattag ctgggtgtgg tggcgggcgc     15313
ctgtaatccc agctactcag gaggctaagg caggagaatc gcttgaaccc tggtggcaga    15373
ggttgcagtg agccgcaatc acgccactgc actccagcct ggatgatggg gtaagactgt    15433
ctcaaaaaaa aaaaaatta gctgagcatg gtggcgtacg cctgtagttc acgccgtcat     15493
ggaggttgag gcagctcctc aggaggctgg ggcagaagga tctctttgct tgagcccagg    15553
agttcaaggc tgcagtgagc tgattgtgcc actgcactcc agcctgaaca aaaacaagac    15613
ctgtctctaa aaacaaacat acagtgttca caatgctgcc caagaagggc cagttttttgc   15673 agctgcccc atgtagcaaa atctggtgct tctgtttcat agacccaaat ggaaattaag     15733
tggatgtgtc ttatttgtaa atttaaaaat attagcgaat gtttgggaat tttttttttt    15793
tttttttttg agacagaatt ttgctcttgt tgcccaggct ggagtgcaat ggcacgatct    15853
cagctcacca caacctctgc ctcccaggtt caagcgattc tcctgcctca gcccccaag     15913
```

-continued

```
aagctgggat tacaggcaca caccaccatg accggctaat tttgtatttt tagtagagat   15973
gaggtttctc ccatgttagg ctggtctcga actcccaacc tcaggtgatc cgcccacctc   16033
ggcctcccaa agtgctggga ttacaggcgt gagccactgc gcccggccta atgtttggga   16093
ttttatgaca tgtcagaagc attacttcag gctttggttt ttaagtaaaa tagcatctaa   16153
tcctctactg agaactcata agaaaacatt ccttatatgt gtggtcttc agttatacaa    16213
gcattttaaa aacaggagaa tgaatataaa tcttaaatca ggcattaaac ccagctgaat   16273
tgttggaagg aggtaagcct gagaccattc ctggacagct tttaccaaca cccatgtaaa   16333
gggggaaagg gtgggcaaga cgtgtgcagc agtctgtatg gacagcttac cagagactga   16393
gggctgaggc agaatcgtga ttcctctgac ccagcagggg cctcctgaca ccgtcagtgc   16453
cttggagatg tgaataccca cctcaccgcc tgaacggcct gttttgcag ttgcccccat     16513
gtagcaaaaa gtaggatgca cggataggac ttcaggggtc tggagaacat gtttttgcat   16573
aaacccagc tttgctctac tgtggcacag agctctggag cctggtttgt gaatgagcct    16633
agctgattct ggcttttctc cctttcttgc tctag ggg atg gac tga acggacagtt   16690
                                       Gly Met Asp
                                               195
ccagaagtgt gactggctaa agtcgatgt ggtcacagct gtatagctgc ttccagtgta    16750
gacggagccc tggcatgtca acagcgttcc tagagaagac aggctggaag atagctgtga   16810
cttctatttt aaagacaatg ttaaacttat aacccacttt aaaatatcta cattaatata   16870
cttgaatgaa aatgtccatt tacacgtatt tgaatggcct tcatatcatc cacacatgaa   16930
tctgcacatc tgtaaatcta cacacggtgc ctttatttcc actgtgcagg ttcccactta   16990
aaaattaaat tggaaagcag gtttcaagga agtagaaaca aaatacaatt ttttttggtaa  17050
aaaaaaatta ctgtttatta aagtacaacc atagaggatg gtcttacagc aggcagtatc   17110
ctgtttgagg aaagcaagaa tcagagaagg aacatacccc ttacaaatga aaaattccac   17170
tcaaaatagg gactatctat cttaatacta aggaaccaac aatcttcctg tttaaaaaac   17230
cacatggcac agagattctg aactaaagtg ctgcactcaa atgatgggaa gtccggcccc   17290
agtacacagg ggcttgactt tttcaacttc gtttcctttg ttggagtcaa aaagaaccac   17350
ttgtggttct aaaaggtgtg aaggtgattt aagggcccag gtcagccact gtttgtttac   17410
aaaatcaggt aactaactgc atacactttt tctctttcca tgacatcaag actttgctaa   17470
agacatgaag ccacgggtgc cagaagctac tgcgatgccc cgggagttag cccctggta    17530
atagctgtaa acttccaatt tctagccata cgctcagctc atccatgcct cagaagtgca   17590
tctggagaga acaggtttct aagcataaaa gatgaaagag cagttggact ttttaaaaat   17650
tcagcaaagt ggttccctct cttagggaca gtcaaaacca agtcacttag gtagtaccaa   17710
aataaataag gaaaagctta gctttagaaa cagtgcaaca ctggtctgct gttccagtgg   17770
taagctatgt cccaggaatc agtttaaaag cacgacagtg gatgctgggt ccatatcaca   17830
cacattgctg tgaacaggaa actcctgtga ccacaacatg aggccactgg agacgcatat   17890
gagtaagggc actgacggac tcatgatttc ttcttaccag atgctttcct gttctttaag   17950
agtttaaaat catcagaaag gaaaaacaaa ctctatattg ttcagcatgc                18000
```

<210> SEQ ID NO 18
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 18
ctttcagaat ctgcctctat                                            20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
agtccatccc atttctggct                                            20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
actgtggtga gtctcccacc                                            20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
agtgtcccag tggcgacctg                                            20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
cacagtccat ggcctgggca                                            20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
ctccgcttcc tcactccgaa                                            20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24 tactcggggag gctgaggcag                                           20
```

```
<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ccgtctttac taagatacaa                                                   20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
tcaagacagt aaatcctgca                                                   20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27 cttttagat cacaggaaaa                                                    20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
gccatttaat tccaagaata                                                   20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
ggcccactga gtggacagct                                                   20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gcatctgttg tttaaagcca                                                   20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 31
acggagcagc cgcatggcac                                                          20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
ggtttcacca tgttggtcag                                                          20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
tctcggctca ctacaacctc                                                          20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
agggacgctg agatctgcgc                                                          20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
ggtctcaaca ggcagaggca                                                          20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
atccctgagg ctggaaccgt                                                          20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
caaacaccag taggtttgtg                                                          20

<210> SEQ ID NO 38
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 38
gaagccaaac accagtaggt                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tgcggaagct gttgtcagaa                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
gggagccagc actggcagct                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
cgggagtggc tgctgcggtt                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gctggacctg ggtttcctca                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
aagcagcccc ttggcaaagg                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
```
agggctggat ctggaagtgg                    20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
agaaggcaga gacattctca                    20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
gcccttcctg gaccttccca                    20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
ctcagtctag aggcaaaggc                    20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
ctgatccgtc tgtgtccagc                    20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 49
aagtagctgg gattacaggc                    20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
ggccctgtac ctagctccca                    20

<210> SEQ ID NO 51
<211> LENGTH: 20
<212> TYPE: DNA
<213> ORGANISM: Artificial Sequence -continued
<220> FEATURE:
<223> OTHER INFORMATION: Antisense Oligonucleotide

<400> SEQUENCE: 51
atcataccac tacactccag                    20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
ttgtatttta agtagagacg                    20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
acaaggccag cccccactgg                    20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
ggcagagaca gagcagactc                    20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
tgcctggcaa tattccggat                    20

<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
cccgacctgg gcgaggtgcc                    20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
gatgctacgg tccatgctgt                    20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
acctcctccg accggctggt                                          20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ccagggcagt ggccaggtcc                                          20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ctagggtagg cctgcagcag                                          20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
tgtctctagg gtaggcctgc                                          20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 62
cggagcaagg acggcgtgtg                                          20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
aaattcactg ttgtgtgaaa                                          20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 64
tgcgtaggtt ctggttaata                                              20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
agagcagtgg gatcacaggc                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
tgttggccag ggtggtctgg                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
agctgtccat acagactgct                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cttctggaac tgtccgttca                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
gttgacatgc cagggctccg                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
atagaagtca cagctatctt                                              20

<210> SEQ ID NO 71
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
tgtagattta cagatgtgca                                                 20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ttaagataga tagtccctat                                                 20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
tccttagtat taagatagat                                                 20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
tagttcagaa tctctgtgcc                                                 20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 75
ccggacttcc catcatttga                                                 20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
aaaagtcaag ccctgtgta                                                  20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
```
aagttgaaaa agtcaagccc                                           20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
gtaaacaaac agtggctgac                                           20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
gtatgcagtt agttacctga                                           20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
tgatgtcatg gaaagagaaa                                           20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
tttagcaaag tcttgatgtc                                           20

<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
tgtctttagc aaagtcttga                                           20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
aacctgttct ctccagatgc                                           20

<210> SEQ ID NO 84
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 84
tagaaacctg ttctctccag                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
tgcttagaaa cctgttctct                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
aatttttaaa aagtccaact                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
tgttgcactg tttctaaagc                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88
agcttaccac tggaacagca                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
gggacatagc ttaccactgg                                               20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
tttaaactga ttcctgggac                                               20
```

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 91
gacccagcat ccactgtcgt                                           20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
gaagaaatca tgagtccgtc                                           20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
gattttaaac tcttaaagaa                                           20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
tagagtttgt ttttccttc                                            20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
aatatagagt ttgttttcc                                            20

<210> SEQ ID NO 96
<211> LENGTH: 30310
<212> TYPE: DNA
<213> ORGANISM: Mus musculus
<220> FEATURE:
<221> NAME/KEY: CDS
<222> LOCATION: (19791)...(19802)
<221> NAME/KEY: CDS
<222> LOCATION: (21160)...(21370)
<221> NAME/KEY: CDS
<222> LOCATION: (24168)...(24307)
<221> NAME/KEY: CDS
<222> LOCATION: (25696)...(25908)
<221> NAME/KEY: CDS
<222> LOCATION: (27235)...(27246)

<400> SEQUENCE: 96

-continued

```
gctcgctttg ggtcatgatg tttcattata ggaatagtaa gccaaactaa gatgatgtct      60
cttcacaaca ttagaaaagt gactaagact ggcctctata gactcatacg tttgaataga     120
actatttggg aaggactagg agatatagcc ttgttggaga aggcgtgtca ctgagggtgg     180
gctttgaggt ttcaaaagcc cagagtcttt ccttctctat ttcctaactg cagatatgga    240
tgcaagctct cagtgattcg ccaccaccat gtctgcctgc ctcttgccac gttccctgcc     300
atgatggtca tggactctaa ctctatgaaa ccataagccc caaattaaaa gaaaaaatt     360 gagagagagt tttttctgt atagacctga ctgttccaga atcactcggt acgacacgac      420
gcgaagctgg ccttgaactc agggatcctc ctgcctctgc cttccaagtg ctgggattaa     480
agggatgtgc caccactact caactaaatg gtttctttta taattcatcg tggtcaaact     540
gttttgtcat ggtaacagaa aaacaactaa gacccagcca tgtctgaggc acacacattt     600
atagatgtac agttaagctt tttctaattc tgtaatggag acagactcac acaatagtac     660
cgcctggaat gttggggatg ggttctaatg cattatctta attcagctca caaagtcaca     720
tgggaatcta catgttcaca tgctgagggt ccctgtcccc agttggtttt tgattgatca     780
ataaagagcc aatggctagt ggttgggcag ggagaaagag gcaggacttt taggatttcc     840
aggcaagaaa ctcaggggag aagatgaaag gactctacca tgagaggggt gtaggacgga    900
ccacaccatt gacagggaag cagaaagatc agacttaaag gcctgccaac atgtaagaat     960
ccagaaaggt gactccaggg gccattgatt gggtctgggg tcacagagat aaaataaaga   1020
tttgtcaagt attaactcaa gaataccaga ggggagtgtg tgctagccta ggggagtttt    1080
ggaaataccc aacgtttgaa ctagtcaaga catctcaaaa tataaaggtt gcatgtatgt    1140
gtctttcatt cgcaaatcca gagagctctg gcgggtggct agaagtgtga tcactttctg    1200
ggaactcaga gtggattaac aattcaccat tacaagtgca gttttggta gggaaggtca     1260 tgtttgtaat ggtgccgagt caccaaagaa agagaaacag ctcttagagt tctatgccag    1320
agggcagagg agcatgcaac ccatccttca gggtttgaca agcagaaggc aggctggtgg    1380
cacagaaaaa aatcatagtt ctggactagt ctgggctaca tagtaacctc tgtcttaacc    1440
ttctcccctt gccctaaagc atctatgatc tgtattggtg ggagcgagag ctgggtggtg   1500
ctgaggttag aaggctccct agctatgggt atttgttaaa atgtgaactc ctccaagaga    1560
tgttataaag tggaaatgtc tagtctcttt ggaaagttag ttatgacaaa tgacattttg    1620
ctggggcaca caagtgaaag gatgtcttcc taaagcagac acaggaaaga atgttttccg    1680
gaagcagaca caggtaaaag gatgttttga tatagcaaac atgtaaaagg acccttgaca    1740
aaggagtata aatatgaccc cacagaccac aggagatgag cactgagcct tggtttggtt    1800
tgttctgcct cgctgttctt cgctaactac atacatgcat tggtttacct tatatagtgt    1860
tgttaatcgc aacttgtgga acaccacca ttgagagaaa gagcagtcca ccaaagaact     1920
gcttgtgagg ttcctacagc agcttgctgc ttctgcggcc tcgcctcagg ctgcttggtg    1980
agcctagcag tttcttcgac tggactgtcc ttgccagttt gtgtgtggtg tctgtctgct    2040
tagaagtctg atctgcagct gctgagttct atttggcgtt tgctacgaga ctgaactgcc    2100
cccaaagaac tatggcaccg tccacttccc ccatagccta attttctctt ctcccacctc    2160
tgctgggtgg tgggctagag gagacgttga acctttatta aaagtaggtt gcaaaaaagt    2220
tgagcctaca aggttatata ttcagaacaa tttctggaat acgattgggt ctacgtggtc    2280
ctagaaatat tcagggcaa agaacacgca gcttgtgtgc gccaggttct gctggctggg     2340
```

-continued

```
tggagagagc gtgccaggta gcacagtgtg ccaggcagca cagagccttt gccctctccc   2400
accctagccc atccctattc cttgtgtcac aggaagtatg gagctaggac cagggaggtg   2460
attgttctgt gatctctaat gtttaggtga gaaatgcccc ttcacaccag acctttgtgt   2520
tcacaccagg ccctgggtt cacaccagtt acacttattt taatgaagct ctttctgtct   2580
aaaatttcta gctcctccct ttaacacttc ctaatttaga gattatttag gctgcacatt   2640
aaaactggaa gtttcactga tagttcagtg gtaaggttgg actcatttaa agtgaaaatt   2700
ggattcccag caaccacacg gtgcccaca gccatctgta atgggatccg atgccctctt   2760
ctgatgtggc tgaagacagc tacaatgtac tcatatacat aaatgaataa ttaaagtgaa   2820
aattggtatg ttccatcttt atgaagttgt gaaatcagtt tccctttttc atttgcattg   2880
attgccaagc acctcggaga gaatcccagt taaaaatatt acgtgttcag gtcatgatca   2940
tgcacgcctt taatcccaga ggcaaaagca ggaggagctc tgtgagttct aggccagcct   3000
ggtttgcata gctagttcca ggccagtcag ggctacatag tgagagcctg tctaaaaaaa   3060
aaaacaaaac aaaaacaaaa cttttttctc attattttcc actttgaaat ctagataatt   3120
cagcttgcat gttttaaatt taaaaactct gtgtgtgtgt gtgtgtgtgt gtgtgtgtgt   3180
tgcctgcata tatgtgcacc acatgtgtgc ctggtcctca tagaggccag aagggggtc    3240 agtcccttgg aattagaata acagatgatt gtcagccacc atatgggtgc taagtactga   3300
acccagatgg atgctctgta agagtgagaa gtgcttttaa ccagtgagcc atctctccaa   3360
cccctgcccc gctgttcatc accaagctct tccactatgt gatttcaagt gtaacttttt   3420
ttttggcggg gggtgggggg gtgggggagt gggggtggg gtgggttgg tttttcgaca    3480 gacagggttt ctctgtatag ccctggctgt cctggaactc actttgtaga ccaggctggc   3540
ctcgaacaga ggcctcccaa gtgcgggat taaaggcgtg cgacaccacg cccggcttca   3600
agtgtaactt ttattgatcg taaaattaga gccatcttcc tttaagaaga attggaaaat   3660
ataaagagga aaagaaacc ctggagatgg ctcggtttgt aaagtacttc atatgcgtaa    3720
gaactggact ttgatccct agcacccatg taaaaactag agtgctgtgt gtatctacaa    3780
ttccattgtt attggtgcac ggtggaagct tcctggagct cacctggcag tcagcctagg   3840
gaaatcacgc gtggagctgg gaagctggtc cactcccctc accccacacc atctcaaaag   3900
aaaaaaaaaa aggtggaaag gtggagagtg atgaaggaaa acactgacct ctggcttaaa   3960
tacacacata cacacacaaa cacacaccaa ccatgtgatt tttttttttt ttttgtctt    4020 ctcagatcca gtttctctgc tcaggaacag caatttccat ggttctattt acttcctcat   4080
acttccagaa ttcactttct tgtttctctt tcacttttgt cactgccacg tgtcctttgg   4140
gggtactggc tggcacttaa gtatatagca ttgggacttc tctggacagg ggaactagct   4200
agcagtttga gattatctgc tagcctcctg gttctttcca cattcatcct tgctgattca   4260
ttccatgacc gagaaccccg caaccccat ccctgccttc cccacaagag tttaaaaatt    4320
ctgcaagcag ctgcgcagga gaaacaatag ggacctccca gcatctctga tagggccgat   4380
tctgacaggg tcactagtct tgagtgtgcc aaccctgcta tgtaatacat caagacaatg   4440
cggagaggtc gggatcaagt atgacacccc atcctcacga gggcaggtcg cccaggcttt   4500
ggggactctg gggagcgcag gttccggtg taccttcctt cctgtccccc gtagcgagcg    4560
ggtaggaccc ttgggtttcc gcaaagtgtg ccagtcgga gggcggagca tccggagggc    4620
ggggctatca caggggcggg gctcccggc gagcacgagg aaaggtaggt ggagtagagc    4680
gccgggccga gtgtggctcc gcaaaccttt gccttagccc gttcgccgcc cggtaccggc   4740
```

```
gcagcggcgt ctgcgtggtg agtatgccca ccctactggg cgccccacg gttcccctct   4800 gggaggacgg ggtcggcacg gagctcagtt tcgtatgcta tcgatccttc gtgatggcgg   4860
ggctcttgcg ccttgatgga ggcggggtgg gggcgccggc cacaggtgc caccgcggag    4920 ctgaggggaa ggcactcact cgaaggcctg gggcgtgcgc cactcgcggt cccctcagc    4980 gctcggtcct ggtccgcttc gggcaggcct cctggtggac ccggggtccc cgcggtcgcg   5040
cgccactcgg caggtgcgcg cagagctgga aggcgggcc tgaggtctcg ctgcgctccg    5100
ctatggccac ccacaaaaat caacaaggaa cggctacagc ccacaaatgg gccctgcaaa   5160
agccctggaa ccccaaccca gggaacacag accttggaag actgcagcga ggggcacctt   5220
tcctacaccc gtgggcacta ctgtgtgcac agctcacact cacgcctgaa ctgtgaggaa   5280
gtggctgacc cctccgcatc tccagtaccc aaaatggttt gaaatgtgc acagactggt    5340 tgctgatgtt tttaaaaagt ttgttgaatg gttggctgaa taaccctata ggattctaga   5400
agaaacccac agccttcagc caccaagtgg cctgggccca caaggattca cacattcgtt   5460
cattcattct ttcgtacatt catttacata ctcaacaaat aagtgtggac cagggacgga   5520
tcagggtaga actttgtggg tggtgagagg ctggaatgaa gagctctgta aaggaccagg   5580
tggtgttgag tatgggactt ctaggctggg cttgaccttc atctgataag ccacatagtt   5640
ctgagtcaag agcatcctga ggacccaggc agggctcccc tactttccca ggctactgcc   5700
tggtgccatg gccaggattg cccttactgg aagactacct tgaagccggg tctaggataa   5760
gctagctgtg gaatggagct gggagaaacc acaagaagga tgtggacttt ccacattcca   5820
gctctaccca accaggagac tttgcagccc tgccccatcc cctgggactt ggtcccaggc   5880
actaccctgg cagtcagctc tgagtgtttc catggggggg ggggggggag cctgatccag   5940
tgctggggct gagttcagag ctttaatac ttgagtgggc tgagctctaa gaaggactcg     6000
gctgggtggt ggtggggaag cagggtggcg attgtgtgtg tcctggcctc tactgcctct   6060
cttgcccaga gagggaatgg cagggaggtt ggcttattac agctgggtta gcaggcattt   6120
cacccactga cgaaaggtgc tatctcctgg ctactgcggg gtggagttgg gtacaggctt   6180
tggtgatggc aagtgaagag aagccggctg gatgtggcat gctctataaa gagatttaag   6240
tagccccaag gtggccaggt tactggagct ctgaaggatg agttgagggt gtacctgaaa   6300
agtgggctgt tagggcagtt actggcgagg ctggggggagg ggaagtgatg ctcacagctt   6360
gaggttacct ggttcctctt atttgcaaga aagaatagcc tacgggggggg ggggggggg    6420 cacagtgctg ggtgcctggc ctccggaagg aaggcctgat gacacagcct tttagacctt   6480
ccgaagggca ctgcatgctt ttccagctgc ccttttgctc tctagtggga agctgagggt    6540
tggggaccca catctaggct gtgttcaaga ccaaagagcc attcctcatc agggagacag   6600
tgaatctgat ggttccaagg atgagagttg gaaactgccc gtccataaga agcccccact   6660
gtgggtctgt ggtcactgga cattttgtct gtggttgtat ctctggccac catttgctgg   6720
gccgtggctg tggagggcag ctggtgtttc tgtttctttc tgggcacgct gcctggctgg   6780
ccagtctcag aggccacatg tattttcct catagtctga aggagacaga taaactgaag   6840
cttcaggttg gagggcagtg atgggcaagt gctatacaga gccttctggg tctgataagc   6900
ccacagagag ctttgttttc cttctcaaat ttcttttttt aaaaggcaga atgtcgccca   6960
gacttgtctc caactcctgc tcaacaatac ctccttgctg ggccgtggtg ggacaccttt   7020
aatccaagaa ctcaggagac agaggccagt ggatctctga gttccagcca gggctgtaca   7080
```

-continued

```
gagaaaccct acaacaaaca aacaaacaaa acaaaacaaa agagtacttc ctgcctcgtc    7140
ctcctaagta ctgggactac agagtgtatc gtttatttta attaactcat gtcgtattac    7200
aataattaga gactagatta ttacttcctt cttcagaaag gtacattggg cagagagggg    7260
ctaatttact tacccagggt ctcaaaatca ggtggaaaac tcccagttta actgtaccac    7320
ctgattctca ggctgcgctc tgcttcccaa gggaggtcca tctgtggagc ccaatagtcc    7380 tcggggtaa ggaacagaga ggatgcccac ggtgttgttt gctttttta cactagggaa     7440 aaccccggcc tagtgtttgt tccatgtgca ttctgccact gagtcagaca tgcacagccc    7500
cttcctgtgg actcttcccc ctagcaggta gagggagaca gggcagctag gtgtatgaat    7560
ggggaagctg gaactttagt gccagggacc tttatggtgg ggtttccccc acgaaccatc    7620
ctggcagatg tccacagcag atgtgtctcc agttcactgt gtcttactct ctgactcttc    7680
tccctcgact ttcgctggtc caaacaggga tatttccgac aaaagggtgg tagcatctac    7740
cctgagctaa acaagatgaa aggcaaccat ttctagaggt gctgccatct tgaaaattga    7800
gttcttagtt ggctttatgg gcatttatcc tcacagacat gttagccttc caaaaacatt    7860
caaacaaaac caagtgaaat caagggaaca gaaaacagag gacaagtgtt ttgtgctctc    7920
ttctcttctc ccacccctct ccctctccct ctcccctcc ccacctcccc ctctctgtct     7980
ctgttggtgt caagtgactt cctcagtcat tctctacatt tccctgtgtg tgacaggact    8040
cttcactcac cgattagta gactggctgg ccagtgggct ctaggatac tccagtctct      8100 gcctcccag cactcggatt ctaggctcag agcactacac tagccttccc atggtcctcg     8160
tgatcccagc tcagacccct atgcttatat aggcctggag tttacagact gagccatatc    8220
ctagccctgg tttgccttaa gttacccttc ttccccagta atgcaaacag acattaggaa    8280
gtacttagga gccaggtgtt tccctactgg ccctggatc ggcctaagaa gggcagtgtg     8340 cttctggca ctatgcctgg aagggtgagg atagctaaac cctggcccag gactgggctg     8400
tgtggaagaa ggcagccaaa tgtagagaga gtttgcctat ctgtgtgtcg tgagacacag    8460
gacagatgct tttttgcagt ttcctgcata gtttctctag tctggaggga tctcctggcc    8520
catagtgggt ctactgtcac catgatggcc acagccaggg aaggcctgta ctgccttagg    8580
ctactgttcc ctccttcagt gacaaaccctt cttgttttt gattttttg ttttgttttg    8640 ttttgttttt ttggttttcg agacagagtt tctctgtata gccctggctg tcctggaact    8700
cactttgtag accaggctgg ccgcgcctag ttttgttttt gcttgttttg ttttgtttta    8760
tgaggcaggg tctcacatat acctgaggct ggttttgtc tcactatata cctgaggcta     8820
gccttgaaca cttgattctc ctgcttccag cttcccaagt gccaggatta caggcttcaa    8880
atctttcttc agaggcagta aaagaacagc tgaagcctgg gtactcgaga ttccagcttg    8940
tgtgatccag agcccttggc tgtaggcttt tacctgagcc agcagtttag ttttcataac    9000
tggtgtatgc atacatgttt ctcctgtagt ggtgctgttc ccaataagta cgttacctca    9060
gcccacctta tgtgtcctca gaacagacag ctagccttcc aaggacaagt gtgactgatg    9120
ggggaaaagg gaccctggaa ctcaccagag ccaccctcct ctagctgagg acatagaaaa    9180
cctttacctg gatttctgtg ggaacttccc aacaggcttt tcctaaccag tcttggaaag    9240
gtgtattgag actgggtgac accatctgga agaggccttg gaacccatag gagcctacca    9300
tgcctcctca gtctggcgtg ttgctatctt atagcataga cctatcttcc cttgagttct    9360
agacaaggca agtttctggc caggacatgg tcttgttttt ctttgagcat cttctagaaa    9420
ccagggagac cataccacaa agcccttact ggactgacta ctgcatgcgc acctccagga    9480
```

```
gcccatctca tcaggcaagg tgactgctgt cctgtctctc tgatggaggc cattgcccct    9540
ttaacaaacg aataaaggtc gctctcccct ctagggtgtg aagacagga aatggctgtt    9600 acccaatgca ggcccactgc cagctctgcc ctcagagcac ggtgcagaca gtccagtcgt    9660
cctccattgg attctctgct gggctaggca cccccagtcc ctctgtggct aagctaagaa    9720
aaagagagag aaaaaaaaaa aaaaaagagt aaagcattgg gggtggggca ggaagagagc    9780
acaggcgtgc aaacatcgaa gagcggcctc tgtgacatct gtctgcgccc ctgttggctc    9840
acccttagga catctgactc cctttctgct agccatcttg tcccacccaa tgcttagata    9900
tttcagaagc ctcggtcctg gtagggagg gaaagcaggt ctctgtatct tataggcctc    9960
agacaaccag gacagccatc ttctgcaggc ctagtgaggc cccagggatg ggcagcttca   10020
gtggcatggt gcacacgccc ttttccacac caccctttgg caagattact ttctgtgcta   10080
atggttaaag gcagaaacct ttgcccacta agcagttgct gcgcccctga gctacgctcg   10140
cgttcttaaa accattgtat tgctggtgtg gtgggtcaag tctgtgatgc cagcacttgg   10200
caggccaagg caggaatgag aaggagaaca agtttcaaag caagcctggg cttcatagta   10260
agaacttgtc tccaaagccc aaagaaaggg ctggagatac aggacagctg cagaaaacca   10320
ggcacagagg ttggcatctg tagacccaac acccggacag tggaggcagg aggatcagaa   10380
gggaagaccg ttcttgcctg aacgtcaagt tctaggccag gctgagggcc atgccaggct   10440
ctctactgtc tatgtatgtg ggtgtttgct tacaccactt tcaaacctgg tgcccaagga   10500
ggccagaaga tggggtcgaa tcccctggaa ctagagttac agacaaatat gagctgctgt   10560
gtaggttctg ggaaatgaac ccaggtcctc tggaagagca gcctgtgctt ttaacaactg   10620 ggccatttt ccggcccata ttcattttta ttacgtgtag ttgtttattt cattatggga   10680
catcccacag catgcacctg gctatcgagac ttgcggaagt cagttctttc tttgcccagt   10740
gtgggtccta aggcttcatt cagttcatgt tggcaggctt gtgcccctg ctttagatgc   10800 cacgtcatct ccagccactc acatattctt gctacccgtt ccttgtcaga tactttgtag   10860
acgtttcctc cccaggctgg atttgaactc actgtgcaga tccgtctgtc ctgttttagc   10920
ttcctggatg ttgagattac agataggaag caccatgtct gactcggttt tatcgtctca   10980
ggagtgtctt ttgaatcata aaagttttca actttgaaga ctacgttagg taatttttt   11040 ttcttttgtt acttgtgcct ctgggctatg tctaagacgt tgcctaatac aagataattg   11100
agacttcctc tcgtgttctc ttttttaaatt ttttatttta taaattatgt gtatcggtgt   11160
tttgactgcg tgtctgtgta ctatgtctgt gtctggtgcc ccaagagcc cagaaaagga   11220 cattgggtct cctgagcctg gagtttcagt tctgagccag tggatcctgg gaatcaaacc   11280
caggtcctct ggaagagtag ccagtactct actgctgaac cagctactct ccagccccca   11340
cccttcttac acttaggtct atctgttttg gtttggtttg gttttaaga atttgttatt   11400 caggggcaag agagatggct cagcagttaa gagcactgac tgctcttcca gaggtcctga   11460
gttcaattcc cagcaaccac atggtggctg aaatgggatc tgatacctc ttctagtgtg   11520 tctgaagaca gtgacagtat actaatacat caaataaata aataaataaa tcttttttaaa   11580 aaataaaaag agaatttgtt attcaaagcc aggtgcatct ctttgggagg ctagcctagt   11640
ctacatagta agtttgagaa cagtcagggc tacatagtga gacctatctc aaaagaaaat   11700
ctgttattca gactggagag atggtgactc agtggttaag agcactggct gctcttcccg   11760
aggacttgtg tgactcctgg catccacatg ggagcacgcc accctctgta actccagttc   11820
```

```
caggtcatct ggcaccctct tctggcctcc acgggcacca ggcacagaga tacatgcagg    11880
caaaacacca tatacatcaa ataaaaataa aatagtttgt tatcttttt  tttgaaaggg    11940 aagacaaagt tttactttta aaaagatta caagcacccc aataacatg taacgagttg    12000 agtcctcgca tctcgtgatt tgggatagga tacactaaca gcagccggaa taagcatacc    12060
atattgactg tcctaaatta tccaggctag agtactgtaa ggctggctgc tacttcatag    12120
gagttgctaa tagctattac tacttttcca taaataacgc ccctgacctt aagaaagta    12180 gaagggaaca gcttactccc tttctttcaa agaattttt  ctacttgact aataaaaaag    12240
tcagcactga tatccattac ttgcagaaga cacaggaaac aggtgacaaa cactccttaa    12300
agacacacaa gataagaaga tggaacttca ggtacatagc aagtcggtac aaaaagctag    12360
atttgatact cttaaaacgt gaagggtcct acaacggcat agagaaataa tttaatgcct    12420
tccagaacag aactcgagct ctgtggaggt ttcctattct ataggggcag atctcatgcc    12480
aacccacaga gcaggcgctt ccacctccta tccctttatg cggtagcttt catggatttc    12540
tggctggatg tcacacacag aggccaagag gtcattcagg actccatccc tgttctgctc    12600
gaagtggttc tggaggacgt tcatcttccc ctgggtctcc tcttccacct cactgctgca    12660
gctgccatga gacccagtg  ctgcagcttc cttggcctct gcagtactgt tcaatttcag    12720
cctggcggct tctttggcct gcttcggcct ccggttcttt cacttgcagg ccttggacac    12780
cttcttggct gcctgcagta gctgctggat gccccgcaac tgactctcgc cattgctgag    12840
gggactttgg gccgagagaa tggcctaaat caaccaacgg ctcaaacata gtcagaagcc    12900
cctccgtttg atgtcattta atgagccttt ctgtgtagct tcaggtcact ccctgaggcc    12960
tggaacaccc tgaatctttt tcagcttttc tgctgaattt ggctgtcacc aggacagact    13020
gctgagggag tgtgttagta ctccagagga gcccagttgt cactatgact ggagcagcgc    13080
agtcttgttt gtggcactgt tgggctatgt ctgctcactg acagttggga tcagttcctc    13140
ttaggtgact cataactgtt gcggtaaatc tcctcccaaa tatgccccgg caatgaaaac    13200
acaacacagt tcatatgaat acatgctgtg cgcctagatt gggcagatct accgctacac    13260
taccatcttc cacatctatg agaccccta  gaacttgcgg tttctccagg ccttgtgctt    13320
ctgctccact ttccccttc  tttctccttg tctgtgtcct ctccctcttc cattttctct    13380
ttgttctctc cccccacctt ccgctccacc ttcccttta  tctgcccaaa cttcagctcc    13440
cctttatttt acaaattaag gtgggaagca ggtttacagg aaatcacctg agtgctgact    13500
atgttcttgt tcacaaccac tctcaggaga acggaattaa catcaaatat aattagcccc    13560
agggctatcg caacacata  acaactatgt cagtgtgatc tggctctatc tgcaagagtt    13620
gaccctctgg tgatgccctg actgagcgtg tcctgcgctt gctaatgctg tggtgctgcc    13680
cctggatggt atgtccacgg ccaacatatg tccaaaagga aagcccctgt cagctgttgt    13740
ttttttcaaa tttatgtcta tgtgtgtgag tattttccct ttttgtatat ctgtgtacca    13800
catgggtgcc cagtgcctgt ggaggcagat gccccagtac tggtgttaca ggcagttaat    13860
atgagctggg aattgaaccc aggtcctttg gaagagcagc cagtgctctt aacttctgag    13920
tcctctctgc agccttctta gcatccattt ttaatcttt  gtatgacatc tggcagaggt    13980
aggaattcat gccttttggg gggatagttg gctatcccag tgtccttggt taaaactgtc    14040
tgttctttcc ctggcggtgg cccgggtcag tgtctgatga actcgatgct cactgctctc    14100
tgatttcttc aaccaggccc gcaccttcat gacgtcatga cgagagctat gggaaggttt    14160
gaaatcagga agtacaagtc tgtcatccac tttgttcctt ttcaagaatg gcgattttg    14220
```

-continued

```
aaaatgtcct ccgcgttcat gtatggattt aggaattgtt tgtcactttc tggagtattt    14280
tttataggaa ttgtgtggag tgctgtagtc tgatagtgtg ttgtctcttc cagcccctga    14340
caggtgcttg ccttccgttg tttatctcaa caagttttgc agttttcgtt tagtgtctaa    14400
tgctcgtata acattcgctc ctaaatgctt tgtgcattaa ttttgttcac ggcactgggg    14460
ttgctctcaa gctctcggta gacgtgtgtt ctactgtgga gatgcaggcc gggtcttagg    14520
attttctgtc tcttggtagc acaataatca tttcatttta ttttgggtta tgagtagtgt    14580
atagaaaaac aggacagcag gggcttgctc tctgctactt tgttttcttc atgaattcct    14640
tgggtgctgt gtgtaaggtc atgtcagatc actgtgttca ggggcttcca aagattcca    14700 ctgtgcagct aagcttgaaa attgctgagg aagctgggca ccacagcacc tacctgtctt    14760
cctgaggcct gcaaggtagc gccaagagta gacctcgctg gcggcgtgcc tggcacccc    14820 cgcctgccat ggaacttgtc ttggtctatg attggtacat gatagacaaa gaggctcttt    14880
tttgtcacat caaggattca gctttgtgac cttaacgttt gttcatcttt atgaataggt    14940
gacatagctg ctttctgttg gggggctggg agagcacacc cggttgctgg actgttttct    15000
ctgcgtcctt ggtcgcaagc tcggttgaac tgttttgtgt ccaaggagaa gaacagcatc    15060
cgttactgga cctgtgagtt tgggtctctt tgtcctgcct ccctctccct gcctgcctat    15120
gtgtgctcgt gtgtgtgtgt gtgtgtgtgt gtgtgtgtgt gtgtgtgtgt gtgtagaggg    15180
aacctcaatt gagaaaatgc ctccatcaga tttgcttgta ggtaagcccg cagggtattt    15240
tcttgattgg tgatggtgtg ggaggtctgg cttactgtgg acagtgccgc tcctgggcag    15300
gtggccctga gttctgtaag aaagagcctg agcaagacat ggaacaagtc agtaagcggc    15360
ccccctccct ggccatgact ccagctcctg cctccaggtt cctgccttga cttccctcag    15420
ggggaggggg acggggacgg gacctgagag ttgttgtgct gagatatgta cttttctccc    15480
caaattgttt ttggtcaagt gttttattac gatagaaagt aaactaaaac acactctccc    15540
cacacacaca ctgactccac cccacacacc gtgaacacag ggccttgagg attccagaca    15600
gccttgtttt gtatttattt tgggacaagg tcttagaaag ttgaacttgt gatcctcctg    15660
cctcagcctt ttgagtagct gggattataa tctgtgtcac cgagtttgtt cttgacctaa    15720
gtagttgaga agagcctttg ctcttgtgta aatgggaaaa ggtgctttag tcacagaggt    15780
ttaggctctg gcttctcact gatgcagcac caactggagg agacattcat acaaattaaa    15840
catttttagg atttttaaaa agtgtgtttc aatgttacat ttggggtaag aatgaaaata    15900
caggaattat gtcggtgcat tgggtgtttt agattgtgtg tgtgtgtgtg tgtgtgtgtg    15960
tgtgtgtgtg tgtgtgcgtg cacagagttt tgaactgaag gttttgctca tgctaagcat    16020
gtgtgctatc acccagttcc tctgaaaaag catctctaat agaaactgcc cattctcggg    16080
cactccgggt agcagagcag cttccgctac tgcgtgttga ctttattgtg ctcttggctt    16140
tttagacatt gtgggaaggg gtggacaaag ctcactgttt atgaaacagt ctgggtttgt    16200
gtcattaatg gataaccatg cctattctcg tgcatgtgac cctgtgttaa ttggatgtcc    16260
taccacctaa tgcttcttac aacacttgat gtttactgtt tccaaaattg gacctagatt    16320
tagaaaaaac aaacaaaac aaacaaaac aaacaaaac ttgatttgct tatttctatt    16380
ttgcatgctg gggatggaat gctcaggcct tactcttgca ggcaggcatt ctaccatcaa    16440
gctgtgttcc cagcccttc aggagcctga cacctaaagc tgagcttggg caatcctgga    16500
aaatctcagg tgtggccatt tgtattgtaa aaagggaaaa ttagggagag atggagggat    16560
```

```
ggatactgga aactgaactc atgtcctctg gtaggataga cagaacactt aaccactgag  16620
ccttctgcaa ccccctttag agagagagag ggagagagag agagagagag agagagagag  16680
agagagagag agagagcgtg catgtgtgtg ttacacacag aggccagaac agctgtcctg  16740
gaactcactt tgtagaccag gctggcctcg aactcagaaa tccgcctgca tctgcctccc  16800
gagttctggg attaaaggcg tgcgccacca cggcccagct ttcaagacaa attcttaacc  16860
gccagtccat ctcgccattc tccaaccagt cccttaaaaa tatttttttt tcaggtgttg  16920
agggtctagc cccgggatac aggcatacta ggcacggctg aagcactgag ctccacacca  16980
caattgggta ttattaccgt cttaccctct aggttattga tatgctgcag aatacagata  17040
ttaatgcagg cacttgtcca caggcctttg tccagtgcag tgtggttatt atcttacagc  17100
tattggcagt cttgcctgcg tctctaagtt cttctgtttc tcatcatctg tgcatatggt  17160
tctttgtcat ttgagttttg tttatttact tatttgtttg tttattttta tggagacaag  17220
gtattgtata gcccagcctg gcttccagct cacagtgttg aagaaggcgg ccgggaactt  17280
ctgcttcctg cgtgctgcag ttacgggtgt gtgccatcgt ctccggcagc ccggggctct  17340
gcatgcatgt gaggcaggca ctctaccaac agggctgcat ctcaagcacc tgggcagttt  17400
tagcacagtt ccttggtttc ccattaagta atgagttaaa tatttaacat atgtccattt  17460
gaaaagatgg aaaacaactt ctcctggtca ctcggcattc atcagccaga agtctgggag  17520
gcttttcttt ctctggatct ccacttggcg gcgttctctg cctgctctgt agcctttgat  17580
aagtggatgg ctgggtgccc tctccgtaat atttatcaca ttttctcgg ttacttgtat  17640
agataaacct cagcagggca ggggcacaag gacacccagc tctgtgtaac agtactttgt  17700
accttcctcc ctattggtgt gtcccgagtc tgcacttcgg gtgggcgggg ttttgtgaag  17760
ttcagagttt tcagctactt cagggctttt ggcttctaca gtacaagaga aacttccagg  17820
ttcctgggag agtgagttgg agtctgagta gtgtgaccca cgtgagctgc tgtccattcc  17880
tcttactcag gacacagctc tctgctcaga aatagctctc tcgtcccaag actccacctg  17940
gtggcttctg gaagaagtgg cctctgtgat ggtggagatt gacagctctg actgtgattg  18000
acagctctga ccaccatgag gtgcatgcaa agtgctttca cacctgtcta ataattctgg  18060
atgtaatgag aaataccaag caaggtgttt ttttttttaa ttagaatttt tattcatcac  18120
tgtgtgtata tgagggaggt gaactcatgc gtatggaggg aagagggacc tggaaccggc  18180
tcctctttga cctttcacat tgttccaggg atggaatgca ggccatctgg cttgctgact  18240
ggcacattca ccagctctct tgcttgcatc tgatcttagc ttttttgagg gacctctaca  18300
ctattttcca tagtagccat attaatttgc attctcagta acagtatata caatgaatgg  18360
atatactttt ttaaccatgc aacaaaacct ttattaacat tttaaacaga tgttccgcta  18420
ttactgaaac tttgtggggg ttggggcggg ggcaggtttc aagacagggt ttttctctga  18480
atagtcctgg ctgccctgaa acttggtttg tagaccaggc tagccgaaaa ctcagggatc  18540
cacctccttc tgcctccagg tgctggaatt aaagttctat accaccaagc ctggctgtac  18600
tgaaacttat aatttctaaa ttcaaatgca caaatggttt tagtgtagag taataccatt  18660
agtgcctacg ggaaatttag gctgaagaac ggagaccatg tgtgggcttg agtcttttct  18720
ggatcaaaaa gagtatggtc atctttcagc tgcttgcctg taacgatgag cgtctgctgg  18780
gtggggtggg aggtgccctc ctaatcctgg gtcttaccct tcacattctc tgtggtatca  18840
gtgggctcta cctcagggtc tgggtcttca caaagattca catcttttt ggggagggg  18900
gtgcgttgag acagcgtttt tctgtgtagt cctggctgtc ctggaactca ctttgtagac  18960
```

-continued

```
caggctggcc ttgaactcag aaatctgcct gcctttgtct cctgagtgct gggattaaag    19020
gcgtgtgcca tcatgcccgg caagactcac atcttaacct gttaatgaag ggattaaagt    19080
gcaaagttca aagcacatca gggcacctag ttataagagc ctctgcactg acaaagctg     19140 ctcgtctgga catcctcaat gaagttcttc aatgactttg gtccagtcag ctatggtaga    19200
tcagaagact tgcatggcgg gcacgtttta ccagccaagc tgccttgccg gctcctccag    19260
atgacatctt cttcccatta agttggaata catactgtgt gctttgcctc atcgtgtgga    19320
aagaggaagt ggttggtggt ttgggggcac tgtggtcctg tagtgtagat gccctgcagt    19380
cttgcaggag tgtgtgacta gctgggaaac ccactaacca gtgtgaggat tagcagcagc    19440
agttcttgtg ggaagcgccg gttggcctga tcagacttac tgaacatggg aagaaagctg    19500
agctctggag aactggcctg gggatgccca ggtcagtgcc agcggaggct tcaaggagga    19560
agactgcaga cctgactcac tgggtctgtg tggagagcaa acaaatgagc caaagccagc    19620
ggtgtggctg ggtgtgcctc agctgcaggt gtgacagtgt cctgtatccc gcggggcccc    19680
gcagaggcat tgctttaggg aacagccacc catggccttg atatgtcctt tttcaggtga    19740
ttccctggac tctgtgagct ggcagtgctt ggagctacac agcttgtgcc  atg gac     19796
                                                        Met Asp
                                                         1 tct gag gttagattct ggtatctttt cattttgttc atcctgggtg tccccgttaa      19852
Ser Glu gcaacctgac ccctcagttg tcaggtctgg caaggtgtac ctcagataat ccaacagagt    19912
tcatctccac tggcacctga tagggactta gtacagaatg ggaaggggg acgtccttcc    19972 agaaggacgg aacggcgtga ctgtcagctt ggtagacata gcaagggcgg cacaaaggcg    20032
ggacagaaaa gatctggaag gttcccttt gccccagtca ggggctgag ctgggctcgg     20092 gcaatagtgc tttctagcct cccagtatct cctgctgtcc tgcagggcct cttgagagtg    20152 ggccctcct ggacaacggt agacttgctg ctgtccctt cttctacctt ggagcaggaa     20212
agctgaggca cagaagaaag tgaaatgctg acattttctc ttacatcttg gcatttgaca    20272
tccttgcccc acatcagaac ttgtatctta ttgtagatgt ttctgacttt atgacaactg    20332
ttatgcacac agttgaggga cattaagtga agcaggtttt gctactacgt ttttttgtac    20392
tacagggact catggaacag gcgttgctga gtgctcctcc tttttttgt ttttgtttt      20452 tttcagaaca ggatttctct gtatagccc ggctgtcctg gaactcactg tgtagaccag     20512
gctggcttcg aactcagaaa tccgcctgcc tctgcctctg cctcccgagt gctgggatta    20572
aaggcgtgcg ccaccacgcc tggcgctaag tgctccttca tagtgctcct acccagggct    20632
gcttttgtac acaccataga actggcagag aggccggtga gcaagaccct ccctgctgcc    20692
tctgatagtg cacatgtccc cctgaaaggc acaggcagag tcggacctgg gtccctgctt    20752
cctagagttt atcaggcatc ctgtgtctgc tcatgaggga gtgaggggaa agaggaaccg    20812
cttgctgcta ggagcacagc ccgtacagtc aggctcagcc ctgaacggaa acatggatgg    20872
aactgaagta gtgacatttg cctgccaccc cagtgtccct gagaccttcc ctcgaagcag    20932
cttccccagt gggtgtcttc aggagggat ctgtagaagg tggctcgatg gccccttggt    20992
gtcttctgtt tggcaagcac accacagcct gttctctgc cctgggcct ctcactaggg      21052 catttagatc ctccgagtta ttgattgtca caggccattg tgactcgggt ccaactgtgc    21112
tctgacccag gctcccgtga gccttcctga ctcccttcc accttag gtc agc aac       21168
                                                    Val Ser Asn
                                                       5
```

| | | | | | | | | | | | | | | | |
|---|---|---|---|---|---|---|---|---|---|---|---|---|---|---|---|
| ggt | tcc | ggc | ctg | ggg | gcc | aag | cac | atc | aca | gac | ctg | ctg | gtg | ttc | ggc | 21216 |
| Gly | Ser | Gly | Leu | Gly | Ala | Lys | His | Ile | Thr | Asp | Leu | Leu | Val | Phe | Gly |
| | 10 | | | | | 15 | | | | 20 | | | | | |

| | | | | | | | | | | | | | | | |
|---|---|---|---|---|---|---|---|---|---|---|---|---|---|---|---|
| ttt | ctc | caa | agc | tct | ggc | tgt | act | cgc | caa | gag | ctg | gag | gtg | ctg | ggt | 21264 |
| Phe | Leu | Gln | Ser | Ser | Gly | Cys | Thr | Arg | Gln | Glu | Leu | Glu | Val | Leu | Gly |
| 25 | | | | | 30 | | | | | 35 | | | | | |

| | | | | | | | | | | | | | | | |
|---|---|---|---|---|---|---|---|---|---|---|---|---|---|---|---|
| cgg | gaa | ctg | cct | gtg | caa | gct | tac | tgg | gag | gca | gac | ctc | gaa | gac | gag | 21312 |
| Arg | Glu | Leu | Pro | Val | Gln | Ala | Tyr | Trp | Glu | Ala | Asp | Leu | Glu | Asp | Glu |
| 40 | | | | 45 | | | | | 50 | | | | | 55 | |

| | | | | | | | | | | | | | | | |
|---|---|---|---|---|---|---|---|---|---|---|---|---|---|---|---|
| ctg | cag | aca | gac | ggc | agc | cag | gcc | agc | cgc | tcc | ttc | aac | caa | gga | aga | 21360 |
| Leu | Gln | Thr | Asp | Gly | Ser | Gln | Ala | Ser | Arg | Ser | Phe | Asn | Gln | Gly | Arg |
| | | | 60 | | | | | 65 | | | | | 70 | | |

| | | | | | | |
|---|---|---|---|---|---|---|
| ata | gag | cca | g | gtaggcctg | gccttgtcca | cctcatccca | aatgtagcct | 21410 |
| Ile | Glu | Pro | | | | |

```
ttactgaccc ccaaaagcta caagggcttt tggagctcag tctctaacct tacattgtca   21470
ggctggtgtg tgtgtgcatg tcatgtgact cctgccttgt gatctgcatg tgactgcccc   21530
cagtaatgtc cagttcatat gacatcgcct gtatcaggac aactaattag aaagttcttc   21590
cttctgatga gtcctgagtt ctcttcaggt ctggacctga ggatcctctc tggaccaata   21650
tttaaaacat ggttttaaa acatatgtcc caaacagtta tagtacagcc aaagtatgga   21710
aattgattgt ctagtttagg cttcattgct gtgaaaagac accatgacca aggcaactgt   21770
tttttgaggg ggaggggggct tcgagacagg gtgtctctgt gtagccctgg ctatcctgga   21830
actcactctg tagaccaggc tggcctcgaa ctcagagatc cgcctgcctc tgcctcccat   21890
gtgctggcta ggttttttat tttttttattt tttttattt cttagttctt tcctgcaact   21950
atcaagtcat tcagaaaaga ggagtcaaga gaggggatga ggtacatttg aaataaaaaa   22010
ctataatgat gattggtcct gcttctgcct ccctagtgct gggattaaag gtgtgcgcca   22070
ccacgcccag cccaaggcaa ttcttataaa ggacaaattt ggttgaggct ggcttacaag   22130
ttcagaaggt cagtccatta acatcatggc aggaagcatg gcagcgtcca ggtaggatgg   22190
tgctggagga agagctgaga gctctgcatc ttgatccagc tgtcatcttc cgggctgcta   22250
ggaggagggt ctgaaagccc actcccacac ttcttccaac aaggacacac ttcctatcag   22310
tgccactatc tgggccaagc atgttcaagc caccatgctg gtcaagatgt tataacccag   22370
aagtgccatc agcttcagct tgtggagttt tggaaagtag caaggcagag tccttcgtcc   22430
tgccattcag atctgggagg tctgggacat tgctagtctg gtcatggctg ccaggtaagc   22490
atccttcaat agccacacag cacctcattt gtgtaggcta gctgaactct caatccagtg   22550
aaaactcctg ccgttagagt cattttgcct cctaaatgaa actttaacat atgtgacttg   22610
ctattaccta aagagatgac cgagtattga agtatcctga ccctcatttc cagataagga   22670
aactgaggca cagcagagaa atggctgacc tcagatcaaa ctgcccatgc agcaggagca   22730
aggctcaacc aagctgctcc ttcatcagtg cagtcacctc ctgctaagcc tgtgtcactc   22790
ggctgctcct agccttcacc tgtcccctgt ccctgtccc catgctgtgt ttacagcaac   22850
tgaggagacc tccctaaagg ctgaggtgca gcgagtgctc agagcgctgt gggcagcatg   22910
caggtgggca tcactgagtt cttcagagtg tacaggcctg gctcgggctc tgctcctcca   22970
gcaggttctg gagctgcatg attttttta aaatgcttgt ctgtctgtct gtctgtctgt   23030
ctgtctgagt atgggtatg cacatgccct agcatatgta tggagtcaga gctggctgtt   23090
ttccttccac catgtgtgtc ctgggatcaa actcaggtca ggatacttca ggactctaag   23150
cactgctgcc tccgatcttg gacacagagg cttcactgcc ctctagtggt tgcaagggag   23210
```

```
accagcagct agtttggctt ccctaccccc ctctggctag tttatttctt ttgagacagg   23270
gccttaccct gcctagcctg aaatttgttg tgttgaccag gctaatcatg aactcccaga   23330
actctgcctg cttctgccaa atgtggttca tttttcaaat gccctgaagt ggtatcttga   23390
gtaggctggg atgtgacagg tattctctac aagctgggtt ttaccatagc cttgtctccg   23450
aagcccacca gtgagccagc cagccaggcc aaaactgaag agaagcgcca ggcagtccag   23510
gaaaggctca ggaagttcag ggcagcggga ggaggctctg gctgtgcgca ggtgtctgtc   23570
actctgtgcc atacccgctt cttcctgcat cagtccatgc cagacttcaa agcctggctt   23630
aagtcacgag actggggatg acgaggcttt gcagacgatc gatcggctgc agattgggag   23690
cagggcaaag tagtggcttc agcaagccag tgagcagctg agtctgccta gaacactcgg   23750
ctagtagtgg atttaaatca cagggaaccg gaagccatgc agttactgtc acctaagcag   23810
aagcagtgag caccagagag gccttgagga gagcagtgtg gtgaccatgt gacaggcatg   23870
gactgaggga gggcctggag taccgctgaa tgctgaagca gttcccact gcattaaagc    23930 agcagtgaca caggcaggac acaggacagg agcaccccca accccccagc ccccgcagca   23990
gcaagcatat aatctgggac aggcctgctt ctccagccag gttctgctac ccaggccttc   24050
cctgcacccg ggaggggcg gcactcatgg tcctcactag gcaggtgcg gaggtaggaa     24110 gtggcctgaa gctgttgaca gaaccattgc tgagtcttgt atttgttgcc taaacag      24167 at  tct gaa agt cag gaa gaa atc atc cac aac att gcc aga cat ctc    24214
    Ser Glu Ser Gln Glu Glu Ile Ile His Asn Ile Ala Arg His Leu
Asp 75              80                  85                  90 gcc caa ata ggc gat gag atg gac cac aac atc cag ccc aca ctg gtg    24262
Ala Gln Ile Gly Asp Glu Met Asp His Asn Ile Gln Pro Thr Leu Val
            95                  100                 105 aga cag cta gcc gca cag ttc atg aat ggc agc ctg tcg gag gaa        24307
Arg Gln Leu Ala Ala Gln Phe Met Asn Gly Ser Leu Ser Glu Glu
        110                 115                 120 gtaagtatga ctctggtctg ggagcccctc ttatgggaca tttcggaagt gtgggacatt   24367
tttccttgtc gaaccagtct ttcccaggaa gtaaaccctg tccttgactg cccgtcagca   24427
tggtctctcc aaagaattta gtcagagtac agagcttagg agtcaggcct ccaggaagat   24487
ccctgaagta cctgatctgt acagatactc agtcttctct tgtggcgaac tccatgtcgt   24547
tcccccaggg tgagcatctg ctcggctgtg tggttagaat cagcacatgg aaaccgatac   24607
aagtccacct cttgctgggt atacggtgaa ggacccaaag ctcgttcctc agcaccgggt   24667
ccttcctaaa gcagaggtgg aggggtggtg gggagagggg agagagagaa accaaacccc   24727
ggggctgtga agtacctgcc caaggaggaa gattctgttc ttaggacttc cagcagctga   24787
aatcgtggct gccctcacca tctagattca ttgtgcctac atacagcctg tctttgctgg   24847
cactctctct acctgccact ctccagtggc tgtcaaagac acacacattt gtcaacagcc   24907
ttgggctcct cctatggggt agattcttta atgtgagcca cagaacctga agctcacttt   24967
ccaccccacc ttgttttttt gttttttgtt ttttgtttt tttttgagg cagggttttct    25027 ctgtatagcc ctggctgtcc tggaactcac tttgtagacc aggctggcct tgaactcaga   25087
aatccacctg cctctgcctc ccgagtgctg ggattaaagg cctgcactcc cctccccatt   25147
ttttaaagag ttaacgttac ctgtttctgc gtgcacctca tgtgtgagta catgagcatg   25207
cttgcaggta catgcattgc catcagatcc cctggagctg aagtttcagg ccattgtgag   25267
ctgttgccta taggtgctgg gaactgaacg ggctcctctg gcagagcagt acatgctctt   25327
caggtccagg ggtccagtat cttcctttcc tgcctgaagg gaagataaca tgtagcccct   25387
```

```
aaagctaagc tcacagtaac atgagcctaa gatgtgctcg tgtccagcca attctgtaag    25447
catctgagtg cagggaagag ctcagacgcc catatgtcag tagtgtgtac aggctactca    25507
ctaaccatgc actggtgagt ctccacgtcc ctctctggtc tgtggagagt gaatcctcta    25567
tcatttcctc cacccaacgt tcttagctat ttaaccacca ctcccctctg aaaggctgct    25627
tcctcctttg gcctgatttg gtctctctga aggaagagca tcagtaaaact gtcttcttta    25687 atgtacag gac aaa agg aac tgc ctg gcc aaa gcc ctt gat gag gtg aag    25737
         Asp Lys Arg Asn Cys Leu Ala Lys Ala Leu Asp Glu Val Lys
                 125                 130                 135 aca gcc ttc ccc aga gac atg gag aac gac aag gcc atg ctg ata atg    25785
Thr Ala Phe Pro Arg Asp Met Glu Asn Asp Lys Ala Met Leu Ile Met
            140                 145                 150 aca atg ctg ttg gcc aaa aaa gtg gcc agt cac gca cca tct ttg ctc    25833
Thr Met Leu Leu Ala Lys Lys Val Ala Ser His Ala Pro Ser Leu Leu
        155                 160                 165 cgt gat gtc ttc cac acg act gtc aac ttt att aac cag aac cta ttc    25881
Arg Asp Val Phe His Thr Thr Val Asn Phe Ile Asn Gln Asn Leu Phe
    170                 175                 180 tcc tat gtg agg aac ttg gtt aga aac gtaagagcca gcagtgacac           25928
Ser Tyr Val Arg Asn Leu Val Arg Asn
185                 190 cagcccctgc ctgcttgcct accctattct aatgcagcag agcctctgct gaagcccctc    25988
tggcccgctc tccttttga ccacccgcag actgagagag caaggctgt ttcacaccac     26048 tgatgggaat cgagcaagct gggggacgt ggagtgttta ggaagatgac taagggctca    26108 gcccctaag tgtgtgtggt gtgcacatgg aagccagagg tcattattgg gtgcctttt    26168 atctcgctct acctatcttt gtgaggtagg gttggttctc cgtgaagtca gaacttgccg    26228
gttaggctaa actagcaaac cctgggcttc cactgcctgc cttcccttcc ctcactgggg    26288
taccagttgt ttaatgtgta ttgatgctct acctgaatgt gtgcctgtgg accatgtgtg    26348
cctgatgcct ggatagccag gagggtgctg catcatctgg gattgagttg caagtggttg    26408
tgagctgcca tatgggtgcc aggaatctga actcggttct tcaggcctct gtagctctta    26468
ctgagccatc tgcacagccc caggtattat gagtaatcag aaagtgacta cacttatttg    26528
tgtgcgcatg ttgctgtggg agcatgtgtg ctacagcata gtcggtcagg acgactctga    26588
ggtcccaggg attgcactca gctcatcagg cttggcactg taagccatgg cccatgactt    26648
agattctttc gaagggcgct tcccgaggat ggagagagaa actgatagga gtaataaatg    26708
agttaagtga gaatcgctgt caagctctcc agtaagcctg aggacgggcc cattgctagg    26768
gtagccctga gtttctattg cgcatgctca ggaagtggtt acacggagct aagcccaagg    26828
tcagtctact gagactgctg gaaaatgacc acgtgttctt agagtcttgt gctctggtta    26888
cacaaaccca agtgggagct ggatggagat acctaacctg cactaggatt ttacaatgtt    26948
tgggatttta gaacctgtca gaaacattat ccgagattct tttgggggga gggggttttt    27008
gtttattctg ggtgaaggca gagtccacat tcccagatgg caatgaatg caaggcaatc    27068 ctcctgcctc agcatctgca ggcatgcacc cccacacctg ggtgggtgga gcagaggaca    27128
ggtctctgtg tgccaggcag gcactgttga ctgagcagca gcccagtgct tgttttctaa    27188
cgcaccgtat cctccaatga gacttactct gctgcctctt tcttag gag atg gac    27243
                                                     Glu Met Asp
                                                             195 tga ggagcccgca caagcccgat ggtgacactg cctccagagg aaccgcgacc           27296
```

```
atggaaagac cttggcctga agacaggtcc cagagaacag ctgtctccct atttccaggt    27356
ggtgggaacc ccaagctggt gattcactgg acatctctgc gttcagcttg agtgtatctg    27416
aagagtttac gccggctcct gcatccacac catgtacctt tgtcctatca gctgtatggg    27476
ttcccacttg ggaatgaaac ttaacagcag gctgtaaggc agaaaagcat ctttgtaatg    27536
ccaagtgact gttcctgaga gccagctctg ggctgtcttc accatgtagg tgggcttctg    27596
tctaaggaga acagcattag gagaggtgca tcggcccatg agcgtgaagt ccacccagcc    27656
tagtggacac tgaagtgctc acaaggcctc cacctgcctt tgtaaaagcc gaatggctga    27716
tctcaaacca tgggaagccc gaccgcccca ccctcctca ccccagcgtt tagctgtttc      27776
aggggtcagc tattatctca agatttctat ccaagtggaa acaaactgaa tcatgcacac    27836
gacttatctg tgtggtgtca gttacactca ggctcttgct acggaatgca agaacaact     27896 cacataccag tgtcaaacag aatgcacaga agagacctaa aacagcagca ggtcactcgg    27956
ttcacaaaag gtgactccca gtcaggtctg acactgtctt ggttgtagag cacagctgcc    28016
atcctctttc cctgggtaac atcacagaag attccatatc aaaagcaaat gttccctccg    28076
cttctgtatt tcagagacaa ggcctcactg tatcctcaag cgttgttacg tcttgtgctg    28136
aactttgctt aaagctggga tcgtcagcac gagccgccac agcctgcaag tattctagtt    28196
ctgaactcat cccagccatg gtggctgtga tggcttgggt gtatcatacc tgtaaattag    28256 tggattttc tttaggaaca tgacctttgg gtgagtataa ttgagaaatt attttaattc      28316
agaaagtact tttcattctg ttctaaaaat atgtgaattg tcttaagtgg tagaaatttg    28376
tttcttcaaa ataaaaggct cttctctaga tgtttgggag agctgtatct ccaaatgacc    28436
tagtacatca gaaggtcaga ccatcccagc agaaacacac agctgtttgg gtcacagttc    28496
tgagggctgt ctttattcca gcgacttcac tagctctgct gactggggac tgaggtgtgg    28556
ttttgtatcc caggaccatg ttttcaacac tgaaaggcaa accaagagtg catgcacttt    28616
tagaatatga aacgtgacct gaaataatcc cccagtaaa tagtggacaa aaagatgagt      28676
caccagttat cataaaatct cgttttattg tcacctccag ggtgcttccc cccatgatgt    28736
tgcttctaaa tgaaagcaca gtttgtagac ttgaattgtc acttgccgat aaagaataga    28796
ttgggcacaa agtagacaac agtatgggaa aggggccgga acaattggaa caattcgcag    28856
taatagagtg agcagatcag acagcagcag tcagctgttg gcgcacactg caaatgaacg    28916
ctgcctgggt taaatgctta tgctagttta gttttttttt tttaagata ggatctcaag      28976 tgtccagggc tagcctttag ctctgagcct agtatggcct tgaacattgt cttcctgcct    29036
tcacccgagt actgggatta caggtacgta ttccatgccc aggatggaac ccaggatttc    29096
atgcaccccg ggcagacatt gatagctaca tctacctgac tctgctatgt taaggataac    29156
cattccagta cctgggggac aagataccag aaccactaac aaactgagtt taatcaagga    29216
gttaggagaa agaggcactt ttagtctcaa ggaagaaaat catgggttgt cagagcaggg    29276
gaaatacagg tccaggagaa aaaggctggc caacagatgg cccatggatg taggaccaca    29336
cagactgttt taggcctcac taagggaggt gtgtagctca ccttcctggg ggaaggcatc    29396
cacaaacctg tcatctcaca atgacaaaac gtggcactgg caagaaaact ccatggatca    29456
aggtgccttc catcaagcat tgggacccac atatcggaag tagagaacaa accaacttca    29516
caagttgtcc tctgactccc acatgcacac tgtggcatgc agccacacac acataaataa    29576
atgaacagct tttcgtatca aaatgtttgc cgaaagctat ccagtaacca gcttattatt    29636
ccgtgccgca aagggcagca ccagagtgac gtgctgacgg aggcccctga gctgactgct    29696
```

```
aatttgggcc tcggcctcaa aggtgtccct gagacggttc tgacctgaga cactgacaac    29756
atcggagggg atgggggcgt gtgtaaacat gagcatggga aggaccctcg ctgcacacag    29816
ggacatggca agccaagttg ggttttcgag gagggctgtg tgaagatgac taggagagct    29876
tccagctctc gaatagcttt ttacagggta gataactaag accacagact cgggtctgat    29936
gggcacagca ctgttctgtg gcagagtttt cactaggaag cactctcgtc agatgagtgg    29996
gatggaaggc tacctcgtta atcctgagcc tgagggccag gaatccaaac agtatctcta    30056
ggtgtccact catccttccg tgtgcctacc ctagaccgat ggccattgca gggaggaagg    30116 accggagggga tcaaaactgc aacaacaaaa acccgacaaa aatgtcaagt ggctggccgc    30176
cttcatatcg ctgcttggtg atgagagctg tgtcagatgg cctgaccttg tttacagcaa    30236
gaagacaaca cattcaccaa caacactaca gaccacaggg tcacccagtg cctaaagggg    30296
cagtggtgca atac                                                     30310
```

<210> SEQ ID NO 97
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 97
cgttgctgac ctcagagtcc                                               20

<210> SEQ ID NO 98
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ctttcagaat ctggctctat                                               20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ggcccggcgc tctactccac                                               20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
gctaaggcaa aggtttgcgg                                               20

<210> SEQ ID NO 101
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 101
cgggtccacc aggaggcctg                                           20

<210> SEQ ID NO 102
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 102
gccatggcac caggcagtag                                           20

<210> SEQ ID NO 103
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 103
gccaggcagc gtgcccagaa                                           20

<210> SEQ ID NO 104
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 104
cttccccatt catacaccta                                           20

<210> SEQ ID NO 105
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 105
cacttgacac caacagagac                                           20

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
gaagcctgta atcctggcac                                           20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
gaccatgtcc tggccagaaa                                           20

<210> SEQ ID NO 108
<211> LENGTH: 20

```
<212> TYPE: DNA
<213> ORGANISM: Artificial Sequence
<220> FEATURE:
<223> OTHER INFORMATION: Antisense Oligonucleotide

<400> SEQUENCE: 108
gtcagtccag taagggcttt                                              20

<210> SEQ ID NO 109
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 109
ttagcttagc cacagaggga                                              20

<210> SEQ ID NO 110
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 110
cgcctgtgct ctcttcctgc                                              20

<210> SEQ ID NO 111
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 111
cccatcttct ggcctccttg                                              20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
ctgaaactcc aggctcagga                                              20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
ctcatggcag ctgcagcagt                                              20

<210> SEQ ID NO 114
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 114
```
cttgaaaagg aacaaagtgg                                              20

<210> SEQ ID NO 115
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 115
tctatacact actcataacc                                              20

<210> SEQ ID NO 116
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 116
ccatcacaga ggccacttct                                              20

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
tccatccctg gaacaatgtg                                              20

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
cagagctcag ctttcttccc                                              20

<210> SEQ ID NO 119
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 119
agctcacaga gtccagggaa                                              20

<210> SEQ ID NO 120
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 120
caagcactgc cagctcacag                                              20

<210> SEQ ID NO 121
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 121
tcagagtcca tggcacaagc                                              20

<210> SEQ ID NO 122
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 122
ttgccaaaca gaagacacca                                              20

<210> SEQ ID NO 123
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 123
gcagagaaac aggctgtggt                                              20

<210> SEQ ID NO 124
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 124
gtctgtgatg tgcttggccc                                              20

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
tggagaaagc cgaacaccag                                              20

<210> SEQ ID NO 126
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 126
acaggcagtt cccgacccag                                              20

<210> SEQ ID NO 127
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 127
ggtctgcctc ccagtaagct                                              20
```

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
cgtctgtctg cagctcgtct                                                    20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
cttttctgaa tgacttgata                                                    20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
cactgatagg aagtgtgtcc                                                    20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
ctcagttgct gtaaacacag                                                    20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
ccacagcgct ctgagcactc                                                    20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
gtcctgaagt atcctgacct                                                    20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 134
gaaataaact agccagaggg                                                 20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
tttcttcctg actttcagaa                                                 20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
ttgggcgaga tgtctggcaa                                                 20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
cgcctatttg ggcgagatgt                                                 20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
gaactgtgcg gctagctgtc                                                 20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
cgccacaaga gaagactgag                                                 20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
aatgtgtgtg tctttgacag                                                 20

<210> SEQ ID NO 141
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
ctacatgtta tcttcccttc                                                   20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
agggctttgg ccaggcagtt                                                   20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
acagcattgt cattatcagc                                                   20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
gagcaaagat ggtgcgtgac                                                   20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
tgtggaagac atcacggagc                                                   20

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
gacagtcgtg tggaagacat                                                   20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
```

```
aggttctggt taataaagtt                                              20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
gtcattttcc agcagtctca                                              20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
gcgggctcct cagtccatct                                              20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
gttctctggg acctgtcttc                                              20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
tcattcccaa gtgggaaccc                                              20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
cagaagccca cctacatggt                                              20

<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
atgcacctct cctaatgctg                                              20

<210> SEQ ID NO 154
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 154
gccgatgcac ctctcctaat                                                    20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
gagcacttca gtgtccacta                                                    20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
agatcagcca ttcggctttt                                                    20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
cccatggttt gagatcagcc                                                    20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
gatagaaatc ttgagataat                                                    20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
caccacacag ataagtcgtg                                                    20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
gtaactgaca ccacacagat                                                    20
```

-continued

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
agcctgagtg taactgacac                                                 20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
gtagcaagag cctgagtgta                                                 20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
ttgcattccg tagcaagagc                                                 20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
agtgacctgc tgctgtttta                                                 20

<210> SEQ ID NO 165
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 165
cttttgatat ggaatcttct                                                 20

<210> SEQ ID NO 166
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 166
aatacagaag cggagggaac                                                 20

<210> SEQ ID NO 167
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 167
gaggccttgt ctctgaaata                                           20

<210> SEQ ID NO 168
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 168
cgtaacaacg cttgaggata                                           20

<210> SEQ ID NO 169
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 169
gctgacgatc ccagctttaa                                           20

<210> SEQ ID NO 170
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 170
cttgcaggct gtggcggctc                                           20

<210> SEQ ID NO 171
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 171
atacttgcag gctgtggcgg                                           20

<210> SEQ ID NO 172
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 172
ctgggatgag ttcagaacta                                           20

<210> SEQ ID NO 173
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 173
cacatatttt tagaacagaa                                           20
```

-continued

```
<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174 gagccttta ttttgaagaa                                                  20
```

ANTISENSE MODULATION OF BH3 INTERACTING DOMAIN DEATH AGONIST EXPRESSION

FIELD OF THE INVENTION

The present invention provides compositions and methods for modulating the expression of BH3 Interacting domain Death agonist. In particular, this invention relates to compounds, particularly oligonucleotides, specifically hybridizable with nucleic acids encoding BH3 Interacting domain Death agonist. Such compounds have been shown to modulate the expression of BH3 Interacting domain Death agonist.

BACKGROUND OF THE INVENTION

Apoptosis, or programmed cell death, is a naturally occurring process that has been strongly conserved during evolution to prevent uncontrolled cell proliferation. This form of cell suicide plays a crucial role in the development and maintenance of multicellular organisms by eliminating superfluous or unwanted cells. However, if this process goes awry, excessive apoptosis results in cell loss and degenerative disorders including neurological disorders such as Alzheimers, Parkinsons, ALS, retinitis pigmentosa and blood cell disorders, while insufficient apoptosis contributes to the development of cancer, autoimmune disorders and viral infections (Thompson, *Science*, 1995, 267, 1456–1462).

The Bcl-2 family of proteins, which includes both positive and negative regulators of apoptosis, act as checkpoints upstream of activated protease cascades orchestrated by caspases and are required for all aspects of cell death (Chao and Korsmeyer, *Annu. Rev. Immunol.*, 1998, 16, 395–419; Kelekar and Thompson, *Trends Cell Biol.*, 1998, 8, 324–330). The Bcl-2 proteins share conserved regions of homology known as Bcl-2 homology domains or BH domains, four of which have been identified to date. It is through the interaction, via dimerization with other Bcl-2 members, of one or more of these domains that the family members exert their pro- or anti-apoptotic effects (Chao and Korsmeyer, *Annu. Rev. Immunol.*, 1998, 16, 395–419; Kelekar and Thompson, *Trends Cell Biol.*, 1998, 8, 324–330).

Anti-apoptotic members of the family include Bcl-2, Bcl-$x_S$, Bcl-$x_L$ and Bcl-w while pro-apoptotic Bcl-2 members include Bax, Bik, Bid, Bim, Hrk and Blk (Kelekar and Thompson, *Trends Cell Biol.*, 1998, 8, 324–330). Three of the pro-apoptotic proteins, Bad, Bid, and Bim, show little similarity to Bcl-2, containing only one BH3 domain (Kelekar and Thompson, *Trends Cell Biol.*, 1998, 8, 324–330). Disclosed in the PCT application WO 99/16787 are the polypeptide and polynucleotide sequence of the BH3 domain found in Bcl-2 family members, specifically BID, and methods to promote apoptosis in a cell by administering an effective amount of the BH3 domain peptide (Korsmeyer, 1999).

Bid (also known as BID or BH3 Interacting domain Death agonist) is a member of the Bcl-2 family and has been shown to dimerize with either Bcl-2, a cell death antagonist, or Bax, a cell death agonist, and can be found in both cytosolic and membrane fractions (Wang et al., *Genes Dev.*, 1996, 10, 2859–2869).

Upon cell surface signaling by a death receptor, it is known that BH3 Interacting domain Death agonist is cleaved by caspase 8 and the C-terminus translocates to the mitochodria and triggers cytochrome c release (Gross et al., *J. Biol. Chem.*, 1999, 274, 1156–1163). It is now known that this process is mediated by the binding of BH3 Interacting domain Death agonist to Bax, with the concomitant induction of a structural change in Bax (Desagher et al., *J. Cell. Biol.*, 1999, 144, 891–901) and is diminished by binding to Bcl-2 (Luo et al., *Cell*, 1998, 94, 481–490).

Due to the integral role played by BH3 Interacting domain Death agonist in apoptosis, the pharmacological modulation of BH3 Interacting domain Death agonist activity and/or expression may therefore be an appropriate point of therapeutic intervention in pathological conditions involving deregulated cell death. Disclosed in the PCT publication, WO 00/11162 is a novel form of BH3 Interacting domain Death agonist (p15 BID) created by the selective cleavage of the cytosolic BH3 Interacting domain Death agonist protein. This 15kD polypeptide, once cleaved, translocates to the mitochondria where it resides as an integral membrane protein and is required for the release of cytochrome c (Gross and Korsmeyer, 2000). Also disclosed are uses of p15 BID and mutant p15 BID polypeptides for the modulation of apoptosis.

Currently, there are no known therapeutic agents which effectively inhibit the synthesis of BH3 Interacting domain Death agonist and to date, investigative strategies aimed at modulating BH3 Interacting domain Death agonist function have involved the use of antibodies, molecules that block upstream entities such as caspase inhibitors (Sun et al., *J. Biol. Chem.*, 1999, 274, 5053–5060) and gene knock-outs in mice (Yin et al., *Nature*, 1999, 400, 886–891).

Disclosed in U.S. Pat. No. 5,955,593 and the PCT application WO 98/09980 are the peptide and nucleic acid sequence of human BH3 Interacting domain Death agonist as well as antibodies, vectors and host cells used to express the BH3 Interacting domain Death agonist protein and reporter constructs used to detect said expression (Korsmeyer, 1999; Korsmeyer, 1998). Antisense oligonucleotides complementary to BH3 Interacting domain Death agonist 15 to 30 nucleotides are also generally disclosed as are methods for treating a disease condition comprising administration of an inhibitory effective amount of purified BH3 Interacting domain Death agonist antisense polynucleotide (Korsmeyer, 1998).

Disclosed in U.S. Pat. No. 5,998,583 are BH3 Interacting domain Death agonist polypeptide and nucleotide derivatives and compositions and uses thereof (Korsmeyer, 1999). there remains, however, a long felt need for additional agents capable of effectively inhibiting BH3 Interacting domain Death agonist function.

Antisense technology is emerging as an effective means for reducing the expression of specific gene products and may therefore prove to be uniquely useful in a number of therapeutic, diagnostic, and research applications for the modulation of BH3 Interacting domain Death agonist expression.

The present invention provides compositions and methods for modulating BH3 Interacting domain Death agonist expression, including modulation of the cleavable form of BH3 Interacting domain Death agonist, p15 BID.

SUMMARY OF THE INVENTION

The present invention is directed to compounds, particularly antisense oligonucleotides, which are targeted to a nucleic acid encoding BH3 Interacting domain Death agonist, and which modulate the expression of BH3 Interacting domain Death agonist. Pharmaceutical and other compositions comprising the compounds of the invention are also provided. Further provided are methods of modulating the expression of BH3 Interacting domain Death agonist in cells or tissues comprising contacting said cells or tissues with one or more of the antisense compounds or compositions of the invention. Further provided are methods of treating an animal, particularly a human, suspected of having or being prone to a disease or condition associated with expression of BH3 Interacting domain Death agonist by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding BH3 Interacting domain Death agonist, ultimately modulating the amount of BH3 Interacting domain Death agonist produced. This is accomplished by providing antisense compounds which specifically hybridize with one or more nucleic acids encoding BH3 Interacting domain Death agonist. As used herein, the terms "target nucleic acid" and "nucleic acid encoding BH3 Interacting domain Death agonist" encompass DNA encoding BH3 Interacting domain Death agonist, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of BH3 Interacting domain Death agonist. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding BH3 Interacting domain Death agonist. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding BH3 Interacting domain Death agonist, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are hereinbelow identified as preferred embodiments of the invention. The target sites to which these preferred sequences are complementary are hereinbelow referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). various salts, mixed salts and free acid forms are also included.

Representative United States patents that teach the preparation of the above phosphorus-containing linkages include, but are not limited to, U.S. Pat. Nos.: 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos.: 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N ($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'—O—$CH_2CH_2OCH_3$, also known as 2'-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'—O—dimethylaminoethoxyethyl or 2'-DMAEOE), i.e., 2'—O—$CH_2$—O—$CH_2$—N($CH_2$)$_2$, also described in examples hereinbelow.

A further prefered modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 3' or 4' carbon atom wherein n is 1 or 2. LNAs and preparation thereof are described in WO 98/39352 and WO 99/14226.

Other preferred modifications include 2'-methoxy (2'—O—$CH_3$), 2'-aminopropoxy (2'-O$CH_2CH_2CH_2NH_2$), 2'-allyl (2'-$CH_2$—CH=$CH_2$), 2'-O-allkyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300;

5,627,053; 5,639,873; 5,646,265; 5,658,873; 5,670,633; 5,792,747; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡—C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3', 2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds.,*Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. Nos. 3,687,808, as well as U.S. Pat. Nos.: 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluores-ceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA,* 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al.,*Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651–3654; Shea et al., *Nucl. Acids Res.,* 1990, 18, 3777–3783), a polyamine or a polyethylene glycol chain (Manoharan et al., *Nucleosides & Nucleotides,* 1995, 14, 969–973), or adamantane acetic acid (Manoharan et al., *Tetrahedron Lett.,* 1995, 36, 3651–3654), a palmityl moiety (Mishra et al., *Biochim. Biophys. Acta,* 1995, 1264, 229–237), or an octadecylamine or hexylamino-carbonyl-oxycholesterol moiety (Crooke et al., *J. Pharmacol. Exp. Ther.,* 1996, 277, 923–937. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos.: 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos.: 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459, 127; 5,521,291; 5,543,158; 5,547,932; 5,583,020; 5,591, 721; 4,426,330; 4,534,899; 5,013,556; 5,108,921; 5,213, 804; 5,227,170; 5,264,221; 5,356,633; 5,395,619; 5,416, 016; 5,417,978; 5,462,854; 5,469,854; 5,512,295; 5,527, 528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of BH3 Interacting domain Death agonist is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding BH3 Interacting domain Death agonist, enabling sandwich and other assays to easily be constructed to exploit this fact. Hybridization of the antisense oligonucleotides of the invention with a nucleic acid encoding BH3 Interacting domain Death agonist can be detected by means known in the art. Such means may include conjugation of an enzyme to the oligonucleotide, radiolabelling of the oligonucleotide or any other suitable detection means. Kits using such detection means for detecting the level of BH3 Interacting domain Death agonist in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoyliphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Prefered bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate, sodium glycodihydrofusidate,. Prefered fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also prefered are combinations of penetration enhancers, for example, fatty acids/salts in combination with bile acids/salts. A particularly prefered combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D, L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999) each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 $\mu$m in diameter. (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms,* Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms,* Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms,* Lieberman, Rieger and Banker (Eds.), 1988, Marcel Dekker, Inc., New York, N.Y., volume 1, p. 335; Idson, in *Pharmaceutical Dosage Forms,* Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms,* Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms,* Lieberman, Rieger and Banker (Eds.), 1988, Marcel Dekker, Inc., New York, N.Y., volume 1, p. 245; Idson, in *Pharmaceutical Dosage Forms,* Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms,* Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems,* Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences,* Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms,* Lieberman, Rieger and Banker (Eds.), 1988, Marcel Dekker, Inc., New York, N.Y., volume 1, p. 245; Block, in *Pharmaceutical Dosage Forms,* Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and triglycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms,* Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms,* Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems,* 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p.92); and perfluorochemical emulsions, such as FC-43. Takahashi et al., *J. Pharm. Pharmacol.,* 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems,* 1991, p.92; Muranishi, *Critical Reviews in Therapeutic Drug Carrier Systems,* 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics,* 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783; Muranishi, *Critical Reviews in Therapeutic Drug Carrier Systems,* 1990, 7, 1–33; Yamamoto et al., *J. Pharm. Exp. Ther.,* 1992, 263, 25; Yamashita et al., *J. Pharm. Sci.,* 1990, 79, 579–583).

Chelating Agents

Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4' isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me-C) nucleotides were synthesized according to published methods [Sanghvi, et. al., *Nucleic Acids Research*, 1993, 21, 3197–3203] using commercially available phosphoramidites (Glen Research, Sterling Va. or ChemGenes, Needham Mass.).

2'-Fluoro amidites

2'-Fluorodeoxyadenosine amidites $2^1$-fluoro oligonucleotides were synthesized as described previously [Kawasaki, et. al., *J. Med. Chem.*, 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3', 5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyrylarabinofurano-sylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta,* 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5). The material was used as is for further reactions (or it can be purified further by column chromatography using a gradient of methanol in ethyl acetate (10–25%) to give a white solid, mp 222–4° C.)

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 9, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL) The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred. at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) nucleoside amidites

2'-(Dimethylaminooxyethoxy) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C. to 0° C. After 1 h the mixture was filtered, the filtrate was washed with ice cold CH$_2$Cl$_2$ and the combined organic phase was washed with water, brine and dried over anhydrous Na$_2$SO$_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was strirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy) ethyl]-5-methyluridine (1.779, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in CH$_2$Cl$_2$). Aqueous NaHCO$_3$ solution (5%, 10 mL) was added and extracted with ethyl acetate (2×20 mL). Ethyl acetate phase was dried over anhydrous Na$_2$SO$_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.399, 6.13 mmol) was added and reaction mixture stirred at 10° C. for 10 minutes. After 10 minutes, the reaction mixture was removed from the ice bath and stirred at room temperature for 2 hrs. To the reaction mixture 5% NaHCO$_3$ (25 mL) solution was added and extracted with ethyl acetate (2×25 mL). Ethyl acetate layer was dried over anhydrous Na$_2$SO$_4$ and evaporated to dryness. The residue obtained was purified by flash column chromatography and eluted with 5% MeOH in CH$_2$Cl$_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'O-[N,N-dimethylaminooxyethyl]-5-methyluridine (1.40 g, 2.4 mmol) and stirred at room temperature for 24 hrs. Reaction was monitored by TLC (5% MeOH in CH$_2$Cl$_2$). Solvent was removed under vacuum and the residue placed on a flash column and eluted with 10% MeOH in CH$_2$Cl$_2$ to get 2'-O-(dimethylaminooxyethyl)-5-methyluridine (766 mg, 92.5%).

5-O-DMT-2'-O-(dimethylaminooxyethyl)-5-methyluridine

2'-O-(dimethylaminooxyethyl)-5-methyluridine (750 mg, 2.17 mmol) was dried over P$_2$O$_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in CH$_2$Cl$_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P$_2$O$_5$ under high vacuum overnight at 40° C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO$_3$ (40 mL). Ethyl acetate layer was dried over anhydrous Na$_2$SO$_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy)nucleoside amidites

2'-(Aminooxyethoxy)nucleoside amidites [also known in the art as 2'-O-(aminooxyethyl)nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-o-(4,4'-dimethoxytrityl)guanosine which may be reduced to provide 2-N-isobutyryl-6-O-diphenylcarbamoyl-2-O-(2-ethylacetyl) 5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2 [2-(Dimethylamino)ethoxy]ethanol (Aldrich, 6.66 g, 50 mmol) is slowly added to a solution of borane in tetrahydrofuran (1 M, 10 mL, 10 mmol) with stirring in a 100 mL bomb. Hydrogen gas evolves as the solid dissolves. O$^2$-,2'-anhydro-5-methyluridine (1.2 g, 5 mmol), and sodium bicarbonate (2.5 mg) are added and the bomb is sealed, placed in an oil bath and heated to 155° C. for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethylaminoethoxy)ethyl)]-5-methyl uridine To 0.5 g (1.3 mmol) of 2'-O-[2(2-N,N-dimethylaminoethoxy)ethyl)]-5-methyluridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH$_2$Cl$_2$ (2×200 mL). The combined CH$_2$Cl$_2$ layers are washed with saturated NaHCO$_3$ solution, followed by saturated NaCl solution and dried over anhydrous sodium sulfate. Evaporation of the solvent followed by silica gel chromatography using MeOH:CH$_2$Cl$_2$:Et$_3$N (20:1, V/V, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture is stirred overnight and the solvent evaporated. The resulting residue is purified by silica gel flash column chromatography with ethyl acetate as the eluent to give the title compound.

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or U.S. Pat. No. 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3'or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 380B, as above. Oligonucleotides are synthesized using the automated synthesizer and 2'-deoxy-5'-dimethoxytrityl-3'-phosphoramidite for the DNA portion and 5'-dimethoxytrityl-2'-O-methyl-3'-O-phosphoramidite for 5' and 3' wings. The standard synthesis cycle is modified by increasing the wait step after the delivery of tetrazole and base to 600 s repeated four times for RNA and twice for 2'-methyl. The fully protected oligonucleotide is cleaved from the support and the phosphate group is deprotected in 3:1 ammonia/ethanol at room temperature overnight then lyophilized to dryness. Treatment in methanolic ammonia for 24 hrs at room temperature is then done to deprotect all bases and sample was again lyophilized to dryness. The pellet is resuspended in 1M TBAF in THF for 24 hrs at room temperature to deprotect the 2' positions. The reaction is then quenched with 1M TEAA and the sample is then reduced to ½ volume by rotovac before being desalted on a G25 size exclusion column. The oligo recovered is then analyzed spectrophotometrically for yield and for purity by capillary electrophoresis and by mass spectrometry.

[2'-O-(2-Methoxyethyl)]-[2'-deoxy]-[2'-O-(Methoxyethyl)]Chimeric Phosphorothioate Oligonucleotides

[2'-O-(2-methoxyethyl)]-[2'-deoxy]-[-2'-O-(methoxyethyl)]chimeric phosphorothioate oligonucleotides were prepared as per the procedure above for the 2'-O-methyl chimeric oligonucleotide, with the substitution of 2'-O-(methoxyethyl)amidites for the 2'-O-methyl amidites.

[2'-O-(2-Methoxyethyl)Phosphodiester]-[2'-deoxy Phosphorothioate]-[2'-O-(2-Methoxyethyl) Phosphodiester]Chimeric Oligonucleotides

[2'-O-(2-methoxyethyl phosphodiester]-[2'-deoxy phosphorothioate]-[2'-O-(methoxyethyl)phosphodiester] chimeric oligonucleotides are prepared as per the above procedure for the 2'-O-methyl chimeric oligonucleotide with the substitution of 2'-O-(methoxyethyl)amidites for the 2'-O-methyl amidites, oxidization with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$p nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a standard 96 well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyldiisopropyl phosphoramidites were purchased from commercial vendors (e.g. PE-Applied Biosystems, Foster City, Calif., or Pharmacia, Piscataway, N.J.). Non-standard nucleosides are synthesized as per known literature or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96 Well Plate Format

The concentration of oligonucleotide in each well was assessed by dilution of samples and UV absorption spectroscopy. The full-length integrity of the individual products was evaluated by capillary electrophoresis (CE) in either the 96 well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following 5 cell types are provided for illustrative purposes, but other cell types can be routinely used, provided that the target is expressed in the cell type chosen. This can be readily determined by methods routine in the art, for example Northern blot analysis, Ribonuclease protection assays, or RT-PCR.

T-24 Cells

The human transitional cell bladder carcinoma cell line T-24 was obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells

The human lung carcinoma cell line A549 was obtained from the American Type Culture Collection (ATCC) (Manassas, Va.). A549 cells were routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence.

NHDF Cells

Human neonatal dermal fibroblast (NHDF) were obtained from the Clonetics Corporation (Walkersville Md.). NHDFs were routinely maintained in Fibroblast Growth Medium (Clonetics Corporation, Walkersville Md.) supplemented as recommended by the supplier. Cells were maintained for up to 10 passages as recommended by the supplier.

HEK Cells

Human embryonic keratinocytes (HEK) were obtained from the Clonetics Corporation (Walkersville Md.). HEKs were routinely maintained in Keratinocyte Growth Medium (Clonetics Corporation, Walkersville Md.) formulated as recommended by the supplier. Cells were routinely maintained for up to 10 passages as recommended by the supplier.

b.END Cells

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds

When cells reached 80% confluency, they were treated with oligonucleotide. For cells grown in 96-well plates, wells were washed once with 200 μL OPTI-MEMM™-1 reduced-serum medium (Gibco BRL) and then treated with 130 μL of OPTI-MEM™-1 containing 3.75 μg/mL LIPOFECTIN™ (Gibco BRL) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of BH3 Interacting Domain Death Agonist Expression Antisense modulation of BH3 Interacting domain Death agonist expression can be assayed in a variety of ways known in the art. For example, BH3 Interacting domain Death agonist mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of BH3 Interacting domain Death agonist can be quantitated in a variety of ways well known in the art, such as immunoprecipitation, Western blot analysis (immunoblotting), ELISA or fluorescence-activated cell sorting (FACS). Antibodies directed to BH3 Interacting domain Death agonist can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1–11.12.9, John Wiley & Sons, Inc., 1997. Preparation of monoclonal antibodies is taught in, for example, Ausubel, F. M. et al., *Current Protocols in Molecular Biology,* Volume 2, pp. 11.4.1–11.11.5, John Wiley & Sons, Inc., 1997.

Immunoprecipitation methods are standard in the art and can be found at, for example, Ausubel, F. M. et al., *Current Protocols in Molecular Biology,* Volume 2, pp. 10.16.1–10.16.11, John Wiley & Sons, Inc., 1998. Western blot (immunoblot) analysis is standard in the art and can be found at, for example, Ausubel, F. M. et al., *Current Protocols in Molecular Biology,* Volume 2, pp. 10.8.1–10.8.21, John Wiley & Sons, Inc., 1997. Enzyme-linked immunosorbent assays (ELISA) are standard in the art and can be found at, for example, Ausubel, F. M. et al., *Current Protocols in Molecular Biology,* Volume 2, pp. 11.2.1–11.2.22, John Wiley & Sons, Inc., 1991.

Example 11

Poly(A)+mRNA Isolation

Poly(A)+mRNA was isolated according to Miura et al., *Clin. Chem.,* 1996, 42, 1758–1764. Other methods for poly(A)+mRNA isolation are taught in, for example, Ausubel, F. M. et al., *Current Protocols in Molecular Biology,* Volume 1, pp. 4.5.1–4.5.3, John Wiley & Sons, Inc., 1993. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates. were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C. was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an PNEASY 96™ kit and buffers purchased from Qiagen Inc. (Valencia Calif.) following the manufacturer's recommended procedures. Briefly, for cells grown on 96-well plates, growth medium was removed from the cells and each well was washed with 200 µL cold PBS. 100 µL Buffer RLT was added to each well and the plate vigorously agitated for 20 seconds. 100 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 15 seconds. 1 mL of Buffer RW1 was added to each well of the RNEASY 96™ plate and the vacuum again applied for 15 seconds. 1 mL of Buffer RPE was then added to each well of the RNEASY 96™ plate and the vacuum applied for a period of 15 seconds. The Buffer RPE wash was then repeated and the vacuum was applied for an additional 10 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 60 µL water into each well, incubating 1 minute, and then applying the vacuum for 30 seconds. The elution step was repeated with an additional 60 µL water.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of BH3 Interacting Domain Death agonist mRNA Levels Quantitation of BH3 Interacting domain Death agonist mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR, in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., JOE, FAM, or VIC, obtained from either Operon Technologies Inc., Alameda, Calif. or PE-Applied Biosystems, Foster City, Calif.) is attached to the 5' end of the probe and a quencher dye (e.g., TAMRA, obtained from either Operon Technologies Inc., Alameda, Calif. or PE-Applied Biosystems, Foster City, Calif.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from PE-Applied Biosystems, Foster City, Calif. RT-PCR reactions were carried out by adding 25 µL PCR cocktail (1×TAQMAN™ buffer A, 5.5 mM MgCl$_2$, 300 µM each of dATP, dCTP and dGTP, 600 µM of dUTP, 100 nM each of forward primer, reverse primer, and probe, 20 Units RNAse inhibitor, 1.25 Units AMPLITAQ GOLD™, and 12.5 Units MuLV reverse transcriptase) to 96 well plates containing 25 µL total RNA solution. The RT reaction was carried out by incubation for 30 minutes at 48° C. Following a 10 minute incubation at 95° C. to activate the AMPLITAQ GOLD™, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, *Analytical Biochemistry*, 1998, 265, 368–374.

In this assay, 175 µL of RiboGreen™ working reagent (RiboGreen™ reagent diluted 1:2865 in 10mM Tris-HCl, 1 mM EDTA, pH 7.5) is pipetted into a 96-well plate containing 25 uL purified, cellular RNA. The plate is read in a CytoFluor 4000 (PE Applied Biosystems) with excitation at 480 nm and emission at 520 nm.

Probes and primers to human BH3 Interacting domain Death agonist were designed to hybridize to a human BH3 Interacting domain Death agonist sequence, using published sequence information (GenBank accession number NM_001196.1, incorporated herein as SEQ ID NO:3). For human BH3 Interacting domain Death agonist the PCR primers were: forward primer: AGAAGACATCATCCGGAATATTGC (SEQ ID NO: 4) reverse primer: GGAGGGATGCTACGGTCCAT (SEQ ID NO: 5) and the PCR probe was: FAM-AGGCACCTCGCCCAGGTCGG-TAMRA (SEQ ID NO: 6) where FAM (PE-Applied Biosystems, Foster City, Calif.) is the fluorescent reporter dye) and TAMRA (PE-Applied Biosystems, Foster City, Calif.) is the quencher dye. For human GAPDH the PCR primers were: forward primer: ACGGATTTGGTCGTAT-TGG (SEQ ID NO: 7) reverse primer: GGCAACAATATC-CACTTTACCAGAGT (SEQ ID NO: 8) and the PCR probe was: 5'JOE-CGCCTGGTCACCAGGGCTGCT-TAMRA 3'(SEQ ID NO: 9) where JOE (PE-Applied Biosystems, Foster City, Calif.) is the fluorescent reporter dye) and TAMRA (PE-Applied Biosystems, Foster City, Calif.) is the quencher dye.

Probes and primers to mouse BH3 Interacting domain Death agonist were designed to hybridize to a mouse BH3 Interacting domain Death agonist sequence, using published sequence information (GenBank accession number U75506, incorporated herein as SEQ ID NO:10). For mouse BH3 Interacting domain Death agonist the PCR primers were: forward primer: TCGAAGACGAGCTGCAGACA (SEQ ID NO:11) reverse primer: TGGCTCTATTCTTCCTTGGT-TGA (SEQ ID NO: 12) and the PCR probe was: FAM-CAGCCAGGCCAGCCGCTCC-TAMRA (SEQ ID NO: 13) where FAM (PE-Applied Biosystems, Foster City, Calif.) is the fluorescent reporter dye) and TAMRA (PE-Applied Biosystems, Foster City, Calif.) is the quencher dye. For mouse GAPDH the PCR primers were: forward primer: GGCAAATTCAACGGCACAGT (SEQ ID NO: 14) reverse primer: GGGTCTCGCTCCTGGAAGCT (SEQ ID NO: 15) and the PCR probe was: 5'JOE-AAGGCCGAGAATGGGAAGCTTGTCATC-TAMRA 3'(SEQ ID NO: 16) where JOE (PE-Applied Biosystems, Foster City, Calif.) is the fluorescent reporter dye) and TAMRA (PE-Applied Biosystems, Foster City, Calif.) is the quencher dye.

Example 14

Northern Blot Analysis of BH3 Interacting Domain Death Agonist mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, OH). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then robed using QUICKHYB™ hybridization solution (Stratagene, La Jolla, Calif.) using manufacturer's recommendations for stringent conditions.

To detect human BH3 Interacting domain Death agonist, a human BH3 Interacting domain Death agonist specific probe was prepared by PCR using the forward primer AGAAGACATCATCCGGAATATTGC (SEQ ID NO: 4) and the reverse primer GGAGGGATGCTACGGTCCAT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

To detect mouse BH3 Interacting domain Death agonist, a mouse BH3 Interacting domain Death agonist specific probe was prepared by PCR using the forward primer TCGAAGACGAGCTGCAGACA (SEQ ID NO:11) and the reverse primer TGGCTCTATTCTTCCTTGGTTGA (SEQ ID NO: 12). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human BH3 Interacting Domain Death Agonist Expression by Chimeric Phosphorothioate Oligonucleotides having 2'-MOE Wings and a Deoxy Gap In accordance with the present invention, a series of oligonucleotides were designed to target different regions of the human BH3 Interacting domain Death agonist RNA, using published sequences (GenBank accession number NM_001196.1, incorporated herein as SEQ ID NO: 3, and rseidues 12001–28000 of GenBank accession number AC006285, incorporated herein as SEQ NO: 17). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human BH3 Interacting domain Death agonist mRNA levels by quantitative real-time PCR as described in other examples herein. Data are averages from two experiments. If present, "N.D." indicates "no data".

Table 1

Inhibition of human BH3 Interacting domain Death agonist mRNA levels by chimeric phosphorothioate oligonucleotides having 2'-MOE wings and a deoxy gap

| ISIS # | REGION | TARGET SEQ ID NO | TARGET SITE | SEQUENCE | %INHIB | SEQ ID NO |
|---|---|---|---|---|---|---|
| 119845 | Coding | 3 | 354 | ctttcagaatctgcctctat | 67 | 18 |
| 119846 | Coding | 3 | 707 | agtccatcccatttctggct | 74 | 19 |
| 119847 | 5'UTR | 17 | 60 | actgtggtgagtctcccacc | 88 | 20 |
| 119848 | 5'UTR | 17 | 2083 | agtgtcccagtggcgacctg | 90 | 21 |
| 119849 | Coding | 17 | 2134 | cacagtccatgcctgggca | 98 | 22 |
| 119850 | Intron | 17 | 3582 | ctccgcttcctcactccgaa | 84 | 23 |
| 119851 | Intron | 17 | 3845 | tactcgggaggctgaggcag | 88 | 24 |
| 119852 | Intron | 17 | 3906 | ccgtctttactaagatacaa | 90 | 25 |
| 119853 | Intron | 17 | 4540 | tcaagacagtaaatcctgca | 93 | 26 |
| 119854 | Intron | 17 | 4580 | cttttagatcacaggaaaa | 89 | 27 |
| 119855 | Intron | 17 | 4987 | gccatttaattccaagaata | 92 | 28 |
| 119856 | Intron | 17 | 5092 | ggcccactgagtggacagct | 93 | 29 |
| 119857 | Intron | 17 | 5373 | gcatctgttgtttaaagcca | 81 | 30 |
| 119858 | Intron | 17 | 5778 | acggagcagccgcatggcac | 85 | 31 |
| 119859 | Intron | 17 | 6999 | ggtttcaccatgttggtcag | 85 | 32 |
| 119860 | Intron | 17 | 7125 | tctcggctcactacaacctc | 75 | 33 |
| 119861 | Intron | 17 | 7369 | agggacgctgagatctgcgc | 92 | 34 |
| 119862 | Intron | 17 | 8083 | ggtctcaacaggcagaggca | 83 | 35 |
| 119863 | Coding | 17 | 8254 | atccctgaggctggaaccgt | 96 | 36 |
| 119864 | Coding | 17 | 8282 | caaacaccagtaggtttgtg | 92 | 37 |
| 119865 | Coding | 17 | 8287 | gaagccaaacaccagtaggt | 86 | 38 |
| 119866 | Coding | 17 | 8318 | tgcggaagctgttgtcagaa | 81 | 39 |
| 119867 | Coding | 17 | 8362 | gggagccagcactggcagct | 79 | 40 |
| 119868 | Coding | 17 | 8418 | cgggagtggctgctgcggtt | 88 | 41 |
| 119869 | Intron | 17 | 9135 | gctggacctgggtttcctca | 86 | 42 |
| 119870 | Intron | 17 | 9353 | aagcagcccttggcaaagg | 94 | 43 |
| 119871 | Intron | 17 | 9424 | agggctggatctggaagtgg | 74 | 44 |
| 119872 | Intron | 17 | 9797 | agaaggcagagacattctca | 93 | 45 |
| 119873 | Intron | 17 | 9875 | gcccttcctggaccttccca | 95 | 46 |
| 119874 | Intron | 17 | 9992 | ctcagtctagaggcaaaggc | 90 | 47 |
| 119875 | Intron | 17 | 10172 | ctgatccgtctgtgtccagc | 96 | 48 |
| 119876 | Intron | 17 | 10643 | aagtagctgggattacaggc | 83 | 49 |
| 119877 | Intron | 17 | 11311 | ggccctgtacctagctccca | 94 | 50 |
| 119878 | Intron | 17 | 11394 | atcataccactacactccag | 18 | 51 |
| 119879 | Intron | 17 | 11641 | ttgtattttaagtagagacg | 85 | 52 |
| 119880 | Intron | 17 | 12649 | acaaggccagccccactgg | 74 | 53 |
| 119881 | Intron | 17 | 12734 | ggcagagacagagcagactc | 77 | 54 |
| 119882 | Coding | 17 | 12795 | tgcctggcaatattccggat | 95 | 55 |
| 119883 | Coding | 17 | 12811 | cccgacctgggcgaggtgcc | 99 | 56 |
| 119884 | Coding | 17 | 12832 | gatgctacggtccatgctgt | 97 | 57 |
| 119885 | Coding | 17 | 12894 | acctcctccgaccggctggt | 98 | 58 |
| 119886 | Coding | 17 | 14042 | ccagggcagtggccaggtcc | 95 | 59 |
| 119887 | Coding | 17 | 14067 | ctagggtaggcctgcagcag | 94 | 60 |
| 119888 | Coding | 17 | 14072 | tgtctctagggtaggcctgc | 94 | 61 |
| 119889 | Coding | 17 | 14151 | cggagcaaggacggcgtgtg | 97 | 62 |
| 119890 | Coding | 17 | 14178 | aaattcactgttgtgtgaaa | 96 | 63 |
| 119891 | Coding | 17 | 14198 | tgcgtaggttctggttaata | 98 | 64 |
| 119892 | Intron | 17 | 14635 | agagcagtgggatcacaggc | 80 | 65 |
| 119893 | Intron | 17 | 14694 | tgttggccagggtggtctgg | 77 | 66 |
| 119894 | Intron | 17 | 16361 | agctgtccatacagactgct | 90 | 67 |
| 119895 | Codina | 17 | 16678 | cttctggaactgtccgttca | 96 | 68 |
| 119896 | 3'UTR | 17 | 16753 | gttgacatgccagggctccg | 98 | 69 |
| 119897 | 3'UTR | 17 | 16798 | ataagaagtcacagctatctt | 95 | 70 |
| 119898 | 3'UTR | 17 | 16933 | tgtagatttacagatgtgca | 68 | 71 |
| 119899 | 3'UTR | 17 | 17176 | ttaagatagatagtccctat | 89 | 72 |
| 119900 | 3'UTR | 17 | 17185 | tccttagtattaagatagat | 84 | 73 |

Table 1-continued

Inhibition of human BH3 Interacting domain Death agonist mRNA levels by chimeric phosphorothioate oligonucleotides having 2'-MOE wings and a deoxy gap

| ISIS # | REGION | TARGET SEQ ID NO | TARGET SITE | SEQUENCE | %INHIB | SEQ ID NO |
|---|---|---|---|---|---|---|
| 119901 | 3'UTR | 17 | 17236 | tagttcagaatctctgtgcc | 62 | 74 |
| 119902 | 3'UTR | 17 | 17267 | ccggacttcccatcatttga | 86 | 75 |
| 119903 | 3'UTR | 17 | 17293 | aaaagtcaagcccctgtgta | 77 | 76 |
| 119904 | 3'UTR | 17 | 17300 | aagttgaaaaagtcaagccc | 59 | 77 |
| 119905 | 3'UTR | 17 | 17391 | gtaaacaaacagtggctgac | 82 | 78 |
| 119906 | 3'UTR | 17 | 17415 | gtatgcagttagttacctga | 86 | 79 |
| 119907 | 3'UTR | 17 | 17439 | tgatgtcatggaaagagaaa | 80 | 80 |
| 119908 | 3'UTR | 17 | 17452 | tttagcaaagtcttgatgtc | 72 | 81 |
| 119909 | 3'UTR | 17 | 17456 | tgtctttagcaaagtcttga | 89 | 82 |
| 119910 | 3'UTR | 17 | 17588 | aacctgttctctccagatgc | 80 | 83 |
| 119911 | 3'UTR | 17 | 17592 | tagaaacctgttctctccag | 85 | 84 |
| 119912 | 3'UTR | 17 | 17596 | tgcttagaaacctgttctct | 90 | 85 |
| 119913 | 3'UTR | 17 | 17632 | aatttttaaaaagtccaact | 24 | 86 |
| 119914 | 3'UTR | 17 | 17731 | tgttgcactgtttctaaagc | 85 | 87 |
| 119915 | 3'UTR | 17 | 17757 | agcttaccactggaacagca | 94 | 88 |
| 119916 | 3'UTR | 17 | 17764 | gggacatagcttaccactgg | 70 | 89 |
| 119917 | 3'UTR | 17 | 17779 | tttaaactgattcctgggac | 89 | 90 |
| 119918 | 3'UTR | 17 | 17802 | gacccagcatccactgtcgt | 36 | 91 |
| 119919 | 3'UTR | 17 | 17904 | gaagaaatcatgagtccgtc | 86 | 92 |
| 119920 | 3'UTR | 17 | 17942 | gattttaaactcttaaagaa | 29 | 93 |
| 119921 | 3'UTR | 17 | 17966 | tagagtttgtttttccttc | 77 | 94 |
| 119922 | 3'UTR | 17 | 17970 | aatatagagtttgttttcc | 50 | 95 |

As shown in Table 1, SEQ ID NOs 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 87, 88, 89, 90, 92 and 94 demonstrated at least 50% inhibition of human BH3 Interacting domain Death agonist expression in this assay and are therefore preferred. The target sites to which these preferred sequences are complementary are herein referred to as "active sites" and are therefore preferred sites for targeting by compounds of the present invention.

Example 16

Antisense Inhibition of Mouse BH3 Interacting Domain Death Agonist Expression by Chimeric Phosphorothioate Oligonucleotides having 2'-MOE Wings and a Deoxy Gap In accordance with the present invention, a second series of oligonucleotides were designed to target different regions of the mouse BH3 Interacting domain Death agonist RNA, using published sequences (GenBank accession number U75506, incorporated herein as SEQ ID NO: 10, and residues 9000–120000 of GenBank accession number AC006945, incorporated herein as SEQ ID NO: 96). The oligonucleotides are shown in Table 2. "Target site" indicates the first (5'-most) nucleotide number on the particular target sequence to which the oligonucleotide binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on mouse BH3 Interacting domain Death agonist mRNA levels by quantitative real-time PCR as described in other examples herein. Data are averages from two experiments. If present, "N.D." indicates "no data".

TABLE 2

Inhibition of mouse BH3 Interacting domain Death agonist mRNA levels by chimeric phosphorothioate oligonucleotides having 2'-MOE wings and a deoxy gap

| ISIS # | REGION | TARGET SEQ ID NO | TARGET SITE | SEQUENCE | %INHIB | SEQ ID NO |
|---|---|---|---|---|---|---|
| 119925 | Start Codon | 10 | 21 | cgttgctgacctcagagtcc | 48 | 97 |
| 119926 | Coding | 10 | 232 | ctttcagaatctggctctat | 32 | 98 |
| 119927 | 5'UTR | 96 | 4669 | ggcccggcgctctactccac | 39 | 99 |
| 119928 | 5'UTR | 96 | 4699 | gctaaggcaaaggtttgcgg | 58 | 100 |
| 119929 | 5'UTR | 96 | 5004 | cgggtccaccaggaggcctg | 42 | 101 |
| 119930 | 5'UTR | 96 | 5693 | gccatggcaccaggcagtag | 71 | 102 |
| 119931 | 5'UTR | 96 | 6758 | gccaggcagcgtgcccagaa | 74 | 103 |
| 119932 | 5'UTR | 96 | 7548 | cttcccattcatacaccta | 61 | 104 |
| 119933 | 5'UTR | 96 | 7977 | cacttgacaccaacagagac | 58 | 105 |

TABLE 2-continued

Inhibition of mouse BH3 Interacting domain Death
agonist mRNA levels by chimeric phosphorothioate
oligonucleotides having 2'-MOE wings and a deoxy gap

| ISIS # | REGION | TARGET SEQ ID NO | TARGET SITE | SEQUENCE | %INHIB | SEQ ID NO |
|---|---|---|---|---|---|---|
| 111934 | 5'UTR | 96 | 8859 | gaagcctgtaatcctggcac | 73 | 106 |
| 119935 | 5'UTR | 96 | 9373 | gaccatgtcctggccagaaa | 83 | 107 |
| 119936 | 5'UTR | 96 | 9439 | gtcagtccagtaagggcttt | 61 | 108 |
| 119937 | 5'UTR | 96 | 9698 | ttagcttagccacagaggga | 80 | 109 |
| 119938 | 5'UTR | 96 | 9768 | cgcctgtgctctcttcctgc | 53 | 110 |
| 119939 | 5'UTR | 96 | 10495 | cccatcttctggcctccttg | 35 | 111 |
| 119940 | 5'UTR | 96 | 11230 | ctgaaactccaggctcagga | 76 | 112 |
| 119941 | 5'UTR | 96 | 12652 | ctcatggcagctgcagcagt | 66 | 113 |
| 119942 | 5'UTR | 96 | 14187 | cttgaaaaggaacaaagtgg | 44 | 114 |
| 119943 | 5'UTR | 96 | 14566 | tctatacactactcataacc | 55 | 115 |
| 119944 | 5'UTR | 96 | 17953 | ccatcacagaggccacttct | 41 | 116 |
| 119945 | 5'UTR | 96 | 18196 | tccatccctggaacaatgtg | 58 | 117 |
| 119946 | 5'UTR | 96 | 19488 | cagagctcagctttcttccc | 68 | 118 |
| 119947 | 5'UTR | 96 | 19741 | agctcacagagtccagggaa | 55 | 119 |
| 119948 | 5'UTR | 96 | 19752 | caagcactgccagctcacag | 59 | 120 |
| 119949 | Coding | 96 | 19782 | tcagagtccatggcacaagc | 61 | 121 |
| 119950 | Intron | 96 | 20989 | ttgccaaacacaagacacca | 3 | 122 |
| 119951 | Intron | 96 | 21013 | gcagacaaacaggctctcgt | 42 | 123 |
| 119952 | Coding | 96 | 21182 | gtctgtgatgtgcttggccc | 63 | 124 |
| 119953 | Coding | 96 | 21205 | tggagaaagccgaacaccag | 57 | 125125 |
| 119954 | Coding | 96 | 21259 | acaggcagttcccgacccag | 71 | 126 |
| 119955 | Coding | 96 | 21282 | ggtctgcctcccagtaagct | 27 | 127 |
| 119956 | Coding | 96 | 21306 | cgtctgtctgcagctcgtct | 89 | 128 |
| 119957 | Intron | 96 | 21950 | cttttctgaatgacttgata | 39 | 129 |
| 119958 | Intron | 96 | 22293 | cactgataggaagtgtgtcc | 54 | 130 |
| 119959 | Intron | 96 | 22835 | ctcagttgctgtaaacacag | 57 | 131 |
| 119960 | Intron | 96 | 22883 | ccacagcgctctgagcactc | 73 | 132 |
| 119961 | Intron | 96 | 23125 | gtcctgaagtatcctgacct | 72 | 133 |
| 119962 | Intron | 96 | 23239 | gaaataaactagccagaggg | 26 | 134 |
| 119963 | Coding | 96 | 24169 | tttcttcctgactttcagaa | 33 | 135 |
| 119964 | Coding | 96 | 24201 | ttgggcgagatgtctggcaa | 55 | 136 |
| 119965 | Coding | 96 | 24208 | cgcctatttgggcgagatgt | 51 | 137 |
| 119966 | Coding | 96 | 24264 | gaactgtgcggctagctgtc | 62 | 138 |
| 119967 | Intron | 96 | 24515 | cgccacaagagaagactgag | 54 | 139 |
| 119968 | Intron | 96 | 24877L aatgt-gtgt-gtctttgacag | 53 | | 140 |
| 119969 | Intron | 96 | 25363 | ctacatgttatcttcccttc | 37 | 141 |
| 119970 | Coding | 96 | 25705 | agggctttggccaggcagtt | 43 | 142 |
| 119971 | Coding | 96 | 25776 | acagcattgtcattatcagc | 67 | 143 |
| 119972 | Coding | 96 | 25814 | gagcaaagatggtgcgtgac | 54 | 144 |
| 119973 | Coding | 96 | 25830 | tgtggaagacatcacggagc | 78 | 145 |
| 119974 | Coding | 96 | 25838 | gacagtcgtgtggaagacat | 48 | 146 |
| 119975 | Coding | 96 | 25858 | aggttctggttaataaagtt | 34 | 147 |
| 119976 | Intron | 96 | 26838 | gtcattttccagcagtctca | 77 | 148 |
| 119977 | Coding | 96 | 27236 | gcgggctcctcagtccatct | 74 | 149 |
| 119978 | 3'UTR | 96 | 27315 | gttctctgggacctgtcttc | 44 | 150 |
| 119979 | 3'UTR | 96 | 27474 | tcattcccaagtgggaaccc | 49 | 151 |
| 119980 | 3'UTR | 96 | 27577 | cagaagcccacctacatggt | 44 | 152 |
| 119981 | 3'UTR | 96 | 27608 | atgcacctctcctaatgctg | 58 | 153 |
| 119982 | 3'UTR | 96 | 27612 | gccgatgcacctctcctaat | 67 | 154 |
| 119983 | 3'UTR | 96 | 27657 | gagcacttcagtgtccacta | 56 | 155 |
| 119984 | 3'UTR | 96 | 27700 | agatcagccattcggctttt | 58 | 156 |
| 119985 | 3'UTR | 96 | 27711 | cccatggtttgagatcagcc | 75 | 157 |
| 119986 | 3'UTR | 96 | 27788 | gatagaaatcttgagataat | 11 | 158 |
| 119987 | 3'UTR | 96 | 27834 | caccacacagataagtcgtg | 65 | 159 |
| 119988 | 3'UTR | 96 | 27842 | gtaactgacaccacacagat | 60 | 160 |
| 119989 | 3'UTR | 96 | 27851 | agcctgagtgtaactgacac | 54 | 161 |
| 119990 | 3'UTR | 96 | 27859 | gtagcaagagcctgagtgta | 48 | 162 |
| 119991 | 3'UTR | 96 | 27868 | ttgcattccgtagcaagagc | 51 | 163 |
| 119992 | 3'UTR | 96 | 27934 | agtgacctgctgctgtttta | 37 | 164 |
| 119993 | 3'UTR | 96 | 28042 | cttttgatatggaatcttct | 50 | 165 |
| 119994 | 3'UTR | 96 | 28067 | aatacagaagcggagggaac | 32 | 166 |
| 119995 | 3'UTR | 96 | 28083 | gaggccttgtctctgaaata | 78 | 167 |
| 119996 | 3'UTR | 96 | 28107 | cgtaacaacgcttgaggata | 63 | 168 |
| 119997 | 3'UTR | 96 | 28145 | gctgacgatcccagctttaa | 38 | 169 |
| 119998 | 3'UTR | 96 | 28167 | cttgcaggctgtggcggctc | 65 | 170 |
| 119999 | 3'UTR | 96 | 28170 | atacttgcaggctgtggcgg | 52 | 171 |

TABLE 2-continued

Inhibition of mouse BH3 Interacting domain Death agonist mRNA levels by chimeric phosphorothioate oligonucleotides having 2'-MOE wings and a deoxy gap

| ISIS # | REGION | TARGET SEQ ID NO | TARGET SITE | SEQUENCE | %INHIB | SEQ ID NO |
|---|---|---|---|---|---|---|
| 120000 | 3'UTR | 96 | 28192 | ctgggatgagttcagaacta | 73 | 172 |
| 120001 | 3'UTR | 96 | 28332 | cacatatttttagaacagaa | 38 | 173 |
| 120002 | 3'UTR | 96 | 28378 | gagccttttattttgaagaa | 60 | 174 |

As shown in Table 2, SEQ ID NOs 97, 98, 99, 100, 101, 102, 103, 104, 105, 106, 107, 108, 109, 110, 111, 112, 113, 114, 115, 116, 117, 118, 119, 120, 121, 123, 124, 125, 126, 128, 129, 130, 131, 132, 133, 135, 136, 137, 138, 139, 140, 141, 142, 143, 144, 145, 146, 147, 148, 149, 150, 151, 152, 153, 154, 155, 156, 157, 159, 160, 161, 162, 163, 164, 165, 166, 167, 168, 169, 170, 171, 172, 173 and 174 demonstrated at least 30% inhibition of mouse BH3 Interacting domain Death agonist expression in this experiment and are therefore preferred. The target sites to which these preferred sequences are complementary are herein referred to as "active sites" and are therefore preferred.sites for targeting by compounds of the present invention.

Example 17

Western Blot Analysis of BH3 Interacting Domain Death Agonist Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to BH3 Interacting domain Death agonist is used, with a radiolabelled or fluorescently labeled secondary antibody directed against the primary antibody species. Bands are visualized using a PHOSPHORIMAGER™ (Molecular Dynamics, Sunnyvale Calif.).

What is claimed is:

1. A compound 8 to 50 nucleobases in length targeted to nucleobases 354 through 373 or nucleobases 707 through 726 of a coding region of a nucleic acid molecule encoding human BH3 Interacting domain Death agonist of SEQ ID NO: 3, nucleobases 60 through 79 or nucleobases 2083 through 2102 of a 5'-untranslated region, nucleobases 2134 through 2153, nucleobases 8254 through 8273, nucleobases 8282 through 8306, nucleobases 8318 through 8332, nucleobases 8362 through 8381, nucleobases 8418 through 8437, nucleobases 12795 through 12830, nucleobases 12832 through 12851, nucleobases 12894 through 12913, nucleobases 14042 through 14061, nucleobases 14067 through 14091, nucleobases 14151 through 14170, nucleobases 14178 through 14217, or nucleobases 16678 through 16697 of a coding region, nucleobases 3582 through 3601, nucleobases 3845 through 3864, nucleobases 3906 through 3925, nucleobases 4540 through 4559, nucleobases 4580 through 4599, nucleobases 4987 through 5006, nucleobases 5092 through 5111, nucleobases 5373 through 5392, nucleobases 5778 through 5797, nucleobases 6999 through 7018, nucleobases 7125 through 7144, nucleobases 7369 through 7388, nucleobases 8083 through 8102, nucleobases 9135 through 9154, nucleobases 9353 through 9372, nucleobases 9424 through 9441, nucleobases 9797 through 9816, nucleobases 9875 through 9894, nucleobases 9992 through 10011, nucleobases 10172 through 10191, nucleobases 10643 through 10662, nucleobases 11311 through 11330, nucleobases 11394 through 11413, nucleobases 11641 through 11660, nucleobases 12649 through 12668, nucleobases 12734 through 12753, nucleobases 14635 through 14652, nucleobases 14694 through 14713, or nucleobases 16361 through 16380 of an intron region, or nucleobases 16753 through 16772, nucleobases 16798 through 16817, nucleobases 16933 through 16952, nucleobases 17176 through 17204, nucleobases 17236 through 17255, nucleobases 17267 through 17286, nucleobases 17293 through 17319, nucleobases 17391 through 17410, nucleobases 17415 through 17454, nucleobases 17439 through 17475, nucleobases 17588 through 17615, nucleobases 17632 through 17651, nucleobases 17731 through 17750, nucleobases 17757 through 17798, nucleobases 17802 through 17821, nucleobases 17904 through 17923, nucleobases 17942 through 17961, nucleobases 17966 through 17989 of a 3'-untranslated region of a nucleic acid molecule encoding human BH3 Interacting domain Death agonist of SEQ ID NO: 17, nucleobases 21 through 40 of a start codon region or nucleobases 232 through 251 of a coding region of a nucleic acid molecule encoding mouse BH3 Interacting domain Death agonist of SEQ ID NO: 10, nucleobases 4669 through 4688, nucleobases 4699 through 4718, nucleobases 5004 through 5023, nucleobases 5693 through 5712, nucleobases 6758 through 6777, nucleobases 7548 through 7567, nucleobases 7977 through 7996, nucleobases 8859 through 8878, nucleobases 9373 through 9392, nucleobases 9439 through 9458, nucleobases 9698 through 9717, nucleobases 9768 through 9785, nucleobases 10495 through 10514, nucleobases 11230 through 11249 nucleobases 12652 through 12671, nucleobases 14187 through 14206, nucleobases 14566 through 14585, nucleobases 17953 through 17972, nucleobases 18196 through 18215, nucleobases 19488 through 19507, nucleobases 19741 through 19771 of a 5'-untranslated region, nucleobases 19782 through 19801, nucleobases 21182 through 21201, nucleobases 21205 through 21224, nucleobases 21259 through 21278, nucleobases 21282 through 21301, nucleobases 21306 through 21325, nucleobases 24169 through 24187, nucleobases 24201 through 24227, nucleobases 24264 through 24283, nucleobases 25705 through 25724, nucleobases 25776 through 25795, nucleobases 25814 through 25877, or nucleobases 27236 through 27255 of a coding region, nucleobases 20989 through 21008, nucleobases 21013 through 21032, nucleobases 21950 through 21969, nucleobases 22293 through 22325, nucleobases 22835 through 22854, nucleobases 22883 through 22902, nucleobases 23125 through 23144, nucleobases 23239 through 23258, nucleobases 24515 through 24534, nucleobases 24877 through 24896, nucleobases 25363 through 25382, or nucleobases 26838 through 26857 of an intron region, or nucleobases 27315 through 27334, nucleobases 27474 through 27493, nucleobases 27577 through 27596, nucleobases 27608 through 27631, nucleobases 27657 through 27676, nucleobases 27700 through 27730, nucleobases 27788 through 27807, nucleobases 27834 through 27887, nucleobases 27934 through 27953, nucleobases 28042 through 28061, nucleobases 28067 through 28102, nucleobases 28107 through 28126, nucleobases 28245 through 28164, nucleobases 28167 through 28189, nucleobases 28192 through 28211, nucleobases 28332 through 28351, or nucleobases 28378 through 28397 of a 3'-untranslated region of a nucleic acid molecule encoding mouse BH3 Interacting domain Death agonist of SEQ ID NO: 96, wherein said compound specifically hybridizes with one of said regions and inhibits the expression of BH3 Interacting domain Death agonist.

2. The compound of claim 1 which is an antisense oligonucleotide.

3. A compound up to 50 nucleobases in length comprising at least an 8-nucleobase portion of SEQ ID NO: 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 87, 88, 89, 90, 92, 94, 97, 98, 99, 100, 101, 102, 103, 104, 105, 106, 107, 108, 109, 110, 111, 112, 113, 114, 115, 116, 117, 118, 119, 120, 121, 123, 124, 125, 126, 128, 129, 130, 131, 132, 133, 135, 136, 137, 138, 139, 140, 141, 142, 143, 144, 145, 146, 147, 148, 149, 150, 151, 152, 153, 154, 155, 156, 157, 159, 160, 161, 162, 163, 164, 165, 166, 167, 168, 169, 170, 171, 172, 173 or 174 which inhibits the expression of BH3 Interacting domain Death agonist.

4. The compound of claim 2 wherein the antisense oligonucleotide comprises at least one modified internucleoside linkage.

5. The compound of claim 4 wherein the modified internucleoside linkage is a phosphorothioate linkage.

6. The compound of claim 2 wherein the antisense oligonucleotide comprises at least one modified sugar moiety.

7. The compound of claim 6 wherein the modified sugar moiety is a 2'-O-methoxyethyl sugar moiety.

8. The compound of claim 2 wherein the antisense oligonucleotide comprises at least one modified nucleobase.

9. The compound of claim 8 wherein the modified nucleobase is a 5-methylcytosine.

10. The compound of claim 2 wherein the antisense oligonucleotide is a chimeric oligonucleotide.

11. A composition comprising the compound of claim 1 and a pharmaceutically acceptable carrier or diluent.

12. The composition of claim 11 further comprising a colloidal dispersion system.

13. The composition of claim 11 wherein the compound is an antisense oligonucleotide.

14. A method of inhibiting the expression of BH3 Interacting domain Death agonist in cells or tissues comprising contacting said cells or tissues in vitro with the compound of claim 1 so that expression of BH3 Interacting domain Death agonist is inhibited.

15. The compound of claim 3 which is an antisense oligonucleotide.

16. The compound of claim 15 wherein the antisense oligonucleotide comprises at least one modified internucleoside linkage.

17. The compound of claim 16 wherein the modified internucleoside linkage is a phosphorothioate linkage.

18. The compound of claim 15 wherein the antisense oligonucleotide comprises at least one modified sugar moiety.

19. The compound of claim 18 wherein the modified sugar moiety is a 2'-O-methoxyethyl sugar moiety.

20. The compound of claim 15 wherein the antisense oligonucleotide comprises at least one modified nucleobase.

21. The compound of claim 20 wherein the modified nucleobase is a 5-methylcytosine.

22. The compound of claim 15 wherein the antisense oligonucleotide is a chimeric oligonucleotide.

23. A composition comprising the compound of claim 3 and a pharmaceutically acceptable carrier or diluent.

24. The composition of claim 23 further comprising a colloidal dispersion system.

25. The composition of claim 23 wherein the compound is an antisense oligonucleotide.

26. A method of inhibiting the expression of BH3 Interacting domain Death agonist in cells or tissues comprising contacting said cells or tissues in vitro with the compound of claim 3 so that expression of BH3 Interacting domain Death agonist is inhibited.

* * * * *